US012558171B2

(12) United States Patent
Khalifa et al.

(10) Patent No.: US 12,558,171 B2
(45) Date of Patent: Feb. 24, 2026

(54) FORCE ESTIMATION AND VISUAL FEEDBACK IN SURGICAL ROBOTICS

(71) Applicant: Vicarious Surgical Inc., Waltham, MA (US)

(72) Inventors: Sammy Khalifa, Waltham, MA (US);
Adam Sachs, Waltham, MA (US);
Michael Eilenberg, Malden, MA (US);
Pankaj Chopra, Medford, MA (US);
Michael Bunne, Rochester, NY (US);
Jeff Bail, Watertown, MA (US)

(73) Assignee: Vicarious Surgical Inc., Waltham, MA (US)

( * ) Notice: Subject to any disclaimer, the term of this patent is extended or adjusted under 35 U.S.C. 154(b) by 632 days.

(21) Appl. No.: 17/744,345

(22) Filed: May 13, 2022

(65) Prior Publication Data

US 2022/0361966 A1     Nov. 17, 2022

Related U.S. Application Data

(60) Provisional application No. 63/193,293, filed on May 26, 2021, provisional application No. 63/188,989, filed on May 14, 2021.

(51) Int. Cl.
*A61B 34/30*     (2016.01)
*A61B 34/00*     (2016.01)
*A61B 34/20*     (2016.01)
*B25J 9/16*      (2006.01)

(52) U.S. Cl.
CPC .............. *A61B 34/30* (2016.02); *A61B 34/20* (2016.02); *A61B 34/71* (2016.02); *B25J 9/1615* (2013.01);
(Continued)

(58) Field of Classification Search
CPC ...... B25J 9/1612; B25J 9/1615; B25J 9/1633; B25J 9/1638; B25J 9/1641; B25J 9/1653;
(Continued)

(56) References Cited

U.S. PATENT DOCUMENTS 8,005,571 B2     8/2011   Sutherland et al.
10,285,765 B2    5/2019   Sachs et al.
(Continued)

FOREIGN PATENT DOCUMENTS

WO        2019094896 A1     5/2019

OTHER PUBLICATIONS

International Preliminary Report on Patentability for Application No. PCT/US2022/029231, dated Nov. 23, 2023, 8 pages.
(Continued)

*Primary Examiner* — Spencer D Patton
(74) *Attorney, Agent, or Firm* — McCarter & English, LLP

(57) ABSTRACT

Described herein are methods and systems for determining force in a robotic surgical system. In some embodiments, a force applied by a robotic component (e.g. a robotic arm, a segment of a robotic arm, or a joint of a robotic arm) is determined. Also described herein are methods and systems for providing visual (e.g., direction and magnitude) feedback to a user without the need for direct haptic feedback. Such visual feedback may be presented to the user in conjunction with haptic feedback.

21 Claims, 19 Drawing Sheets
(4 of 19 Drawing Sheet(s) Filed in Color)

(52) U.S. Cl.
CPC ........... *B25J 9/1653* (2013.01); *B25J 9/1694*
(2013.01); *A61B 2034/2055* (2016.02)

(58) Field of Classification Search
CPC ....... B25J 9/1694; B25J 9/1697; A61B 34/00;
A61B 34/10; A61B 34/30–71; A61B
34/76; A61B 34/77; A61B 2034/101–104;
A61B 2034/301–715; A61B
2034/2046–2065; A61B 2090/064–067;
A61B 2017/00398
See application file for complete search history.

(56) References Cited

U.S. PATENT DOCUMENTS

| | | | |
|---|---|---|---|
| 10,532,466 B2 | 1/2020 | Schaible et al. | |
| 2007/0018958 A1 | 1/2007 | Tavakoli et al. | |
| 2016/0331482 A1 | 11/2016 | Hares | |
| 2017/0080574 A1 | 3/2017 | Kuroda et al. | |
| 2019/0328245 A1* | 10/2019 | Albu ................... | A61B 5/0215 |
| 2020/0206961 A1 | 7/2020 | Tümerdem | |
| 2020/0222138 A1 | 7/2020 | Diolaiti | |
| 2020/0405403 A1* | 12/2020 | Shelton, IV ....... | A61B 17/3421 |
| 2021/0177548 A1* | 6/2021 | Shanjani ................ | A61C 13/34 |
| 2022/0402130 A1* | 12/2022 | Takagi ................... | A61B 1/005 |
| 2024/0108427 A1* | 4/2024 | Peine .................... | A61B 34/71 |

OTHER PUBLICATIONS

International Search Report and Written Opinion, PCT/US22/29231
(Sep. 21, 2022) (11 pgs).

* cited by examiner

FORCE ESTIMATION AND VISUAL FEEDBACK IN SURGICAL ROBOTICS

CROSS-REFERENCE

This application claims the benefit under 35 U.S.C. § 119(e) of U.S. Provisional Patent Application No. 63/188,989, filed on May 14, 2021, and U.S. Provisional Patent Application No. 63/193,293, filed on May 26, 2021, each of which is incorporated by reference herein in its entirety.

BACKGROUND

Surgical robots are used in a number of surgical procedures. Surgical robots include hardware and software components.

SUMMARY

In an aspect, the present disclosure provides a computer-implemented method for determining an output force applied by an output joint of a cable-driven surgical robot, comprising: applying, using a motor of the cable-driven surgical robot, a motor force to a cable communicatively connected to the output joint of the cable-driven surgical robot; identifying a set of kinematic parameters of a lumped-parameter model, in response to the motor force, wherein the lumped-parameter model is indicative of an interactive structural configuration of the cable-driven surgical robot, wherein the set of parameters comprises at least one joint parameter, at least one cable parameter, and at least one motor parameter, wherein the identifying comprises (i) measuring parameters using at least one sensor or (ii) estimating parameters via dynamical simulation; and determining an output force applied by the output joint, wherein the determining comprises performing a dynamical simulation using the set of kinematic parameters.

In some embodiments, the method further comprises computer processing the motor force and the output force. In some embodiments, the computer processing comprises comparing the motor force and the output force. In some embodiments, the computer processing comprises determining a difference between the motor force and the output force. In some embodiments, the method further comprises adjusting the motor force applied to the cable based at least in part on the computer processed motor force, output force, or both. In some embodiments, the adjusting is performed in real time or in substantially real time.

In some embodiments, the set of kinematic parameters comprises at least one static parameter and one dynamic parameter. In some embodiments, the at least one static parameter comprises position, orientation, length, width, height, diameter, or stiffness. In some embodiments, the at least one static parameter comprises at least one of: a static parameter of the motor, a static parameter of the cable, and a static parameter of the output joint. In some embodiments, the at least one static parameter comprises at least two of: a static parameter of the motor, a static parameter of the cable, and a static parameter of the output joint. In some embodiments, the at least one static parameter comprises each of: a static parameter of the motor, a static parameter of the cable, and a static parameter of the output joint. In some embodiments, the at least one dynamic parameter comprises damping, fraction, velocity, acceleration, or inertia. In some embodiments, the at least one dynamic parameter comprises at least one of: a dynamic parameter of the motor, a dynamic parameter of the cable, and a dynamic parameter of the output joint. In some embodiments, the at least one dynamic parameter comprises at least two of: a dynamic parameter of the motor, a dynamic parameter of the cable, and a dynamic parameter of the output joint. In some embodiments, the at least one dynamic parameter comprises each of: a dynamic parameter of the motor, a dynamic parameter of the cable, and a dynamic parameter of the output joint.

In some embodiments, the method further comprises applying the output force to a body part of a subject using the output joint. In some embodiments, the method further comprises determining a reaction force exerted by the body part of the subject on the output joint. In some embodiments, the method further comprises adjusting the motor force applied to the end effector based at least in part on the determined reaction force. In some embodiments, the at least one sensor comprises one or more of a camera, a position sensor, an accelerometer, a magnetic sensor, light sensor, or combinations thereof.

In some embodiments, the method further comprises generating an audiovisual representation of the output force, wherein the audiovisual representation comprises a virtual object comprising at least one discrete or continuous variable that is dynamically changing based at least in part on the determined output force. In some embodiments, the method further comprises displaying the virtual object on a screen or display. In some embodiments, the method further comprises generating and displaying an overlay of the virtual object onto an image captured by at least one camera.

In some embodiments, the cable-driven surgical robot is partially or wholly inside of a cavity of a body of a subject. In some embodiments, the cable-driven surgical robot is wholly inside of a cavity of a body of a subject.

In another aspect, the present disclosure provides a computer-implemented system for determining an output force applied by an output joint, comprising: a cable-driven surgical robot comprising a motor, the output joint, and a cable communicatively connected to the output joint; and one or more computer processors operatively coupled to the cable-driven surgical robot, wherein the one or more computer processors are individually or collectively programmed to: apply, using the motor, a motor force to the cable; identify a set of kinematic parameters of a lumped-parameter model, in response to the motor force, wherein the lumped-parameter model is indicative of an interactive structural configuration of the cable-driven surgical robot, wherein the set of parameters comprises at least one joint parameter, at least one cable parameter, and at least one motor parameter, wherein the identifying comprises (i) measuring parameters using at least one sensor or (ii) estimating parameters via dynamical simulation; and determine an output force applied by the output joint, wherein the determining comprises performing a dynamical simulation using the set of kinematic parameters.

In another aspect, the present disclosure provides a computer-implemented method for operating a cable-driven surgical robotic system within a body cavity of a subject, comprising: controlling an operation of the surgical robotic system, wherein the cable-driven surgical robotic system comprises a motor, an output joint, a cable communicatively coupling the motor and the output joint, and at least one sensor; and receiving feedback from the surgical robotic system, wherein the feedback comprises an audiovisual representation of a state of the surgical operation, wherein the audiovisual representation comprises a virtual object comprising at least one discrete or continuous variable that is dynamically changing based on the state of the surgical operation.

In some embodiments, the method further comprises adjusting operation of the surgical robotic system based at least in part on the feedback received. In some embodiments, the method further comprises displaying the virtual object on a screen or display. In some embodiments, the method further comprises generating and displaying an overlay of the virtual object onto an image captured by at least one camera.

In another aspect, the present disclosure provides a computer-implemented system comprising: a cable-driven surgical robot comprising a motor, the output joint, a cable communicatively connected to the output joint, and at least one sensor; and one or more computer processors operatively coupled to the cable-driven surgical robot, wherein the one or more computer processors are individually or collectively programmed to: control surgical operation of the surgical robotic system within a body cavity of a subject; and receive feedback from the surgical robotic system, wherein the feedback comprises an audiovisual representation of a state of the surgical operation, wherein the audiovisual representation comprises a virtual object comprising at least one discrete or continuous variable that is dynamically changing based on the state of the surgical operation.

In another aspect, the present disclosure provides a method for operating a cable-driven surgical robotic system within a body cavity of a subject, comprising: controlling a cable-driven surgical robot based on a user input, wherein the cable-driven surgical robotic system comprises a motor, an output joint, a cable communicatively coupling the motor and the output joint, and at least one sensor; determining a state of the surgical operation, based at least in part on sensor data obtained from the at least one sensor; and generating a feedback comprising an audiovisual representation of the state of the surgical operation, wherein the audiovisual representation comprises a virtual object comprising at least one discrete or continuous variable that is dynamically changing based at least in part on the state of the surgical operation.

In some embodiments, the method further comprises determining a difference between the state of the surgical operation and a desired state of the surgical operation, and generating the audiovisual representation based on the determined difference. In some embodiments, the method further comprises displaying the virtual object on a screen or display. In some embodiments, the method further comprises generating and displaying an overlay of the virtual object onto an image captured by at least one camera.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

5

Figure 1:
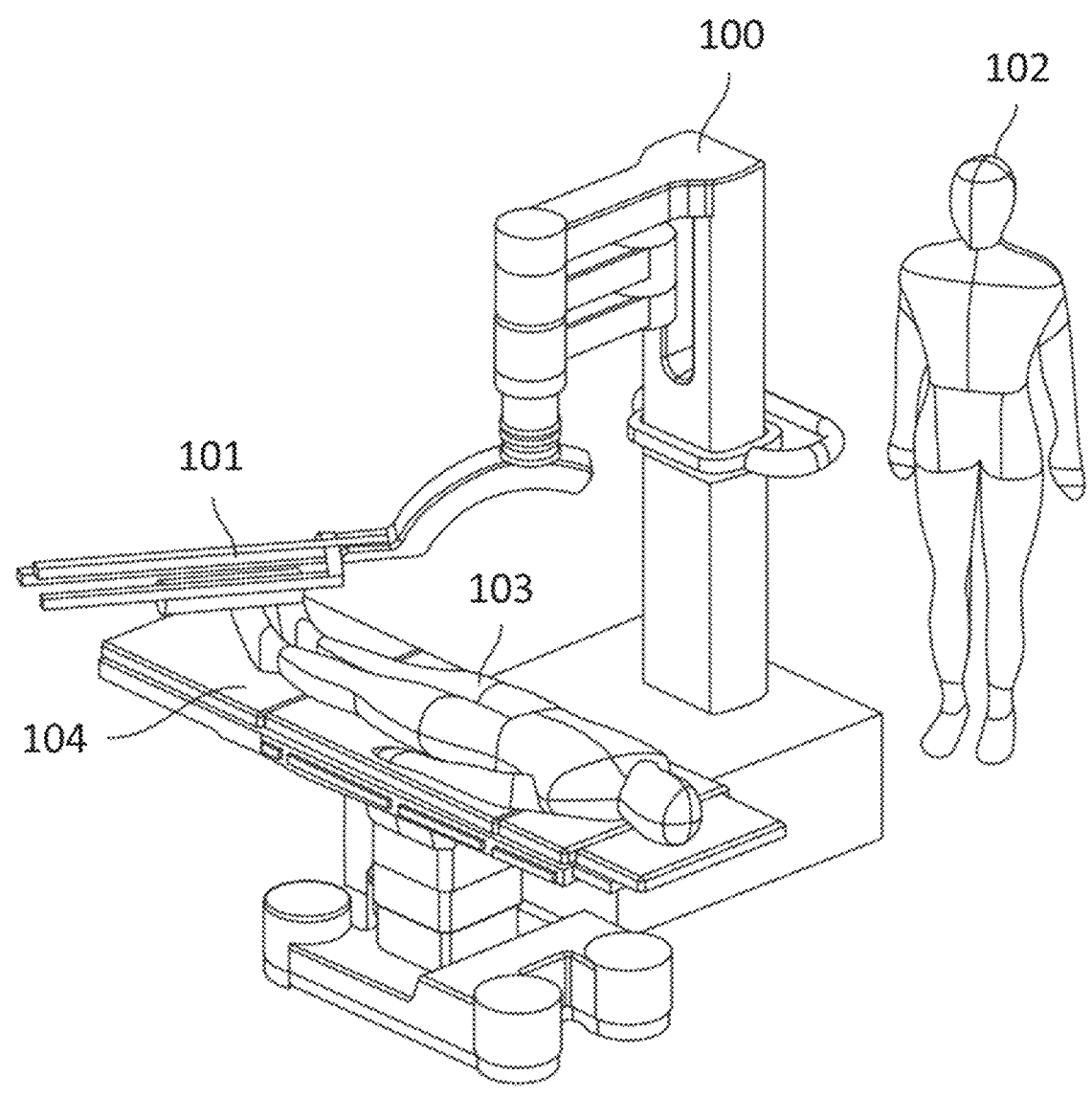
FIGS. 1-3 illustrate examples of a robotic assembly positioned relative to a subject (e.g., patient) receiving a surgical procedure and a medical professional performing the surgical procedure with the assistance of the robotic assembly.

FIGS. 16A-16D show examples of an audiovisual representation of a robot error tracking approach which is performed during a surgical operation within an internal cavity of a cadaver.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed. It is intended that the following claims define the scope of the disclosure and that methods and structures within the scope of these claims and their equivalents be covered thereby.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Any systems, methods, software, and platforms described herein are modular and not limited to sequential operations. Accordingly, terms such as "first" and "second" do not necessarily imply priority, order of importance, or order of acts.

As used herein, the term "about" or "approximately" generally refers to within an acceptable error range for the particular value as determined by one of ordinary skill in the art, which may depend in part on how the value is measured or determined, e.g., the limitations of the measurement system. For example, "about" can refer to within 1 or more than 1 standard deviation, per the practice in the given value. Where particular values are described in the application and claims, unless otherwise stated the term "about" should be assumed to mean an acceptable error range for the particular value.

Although an exemplary embodiment is described as using a plurality of units to perform an exemplary process, it is understood that the exemplary processes may also be performed by one or plurality of software modules. Additionally, it is understood that the term controller/control unit, as used herein, generally refers to a hardware device that includes a memory and a processor and is specifically programmed to execute one or more of the processes described herein. The memory may be configured to store the software modules, and the processor may be configured to execute instructions of the software modules to perform one or more processes disclosed herein.

The present disclosure provides methods and systems for determining force applied by a component of a robotic assembly. In some embodiments, the method or system comprises determining a force acting on a joint of a robotic assembly such as a joint of a robot used in a surgical procedure.

Robotic Assembly

Figure 2:
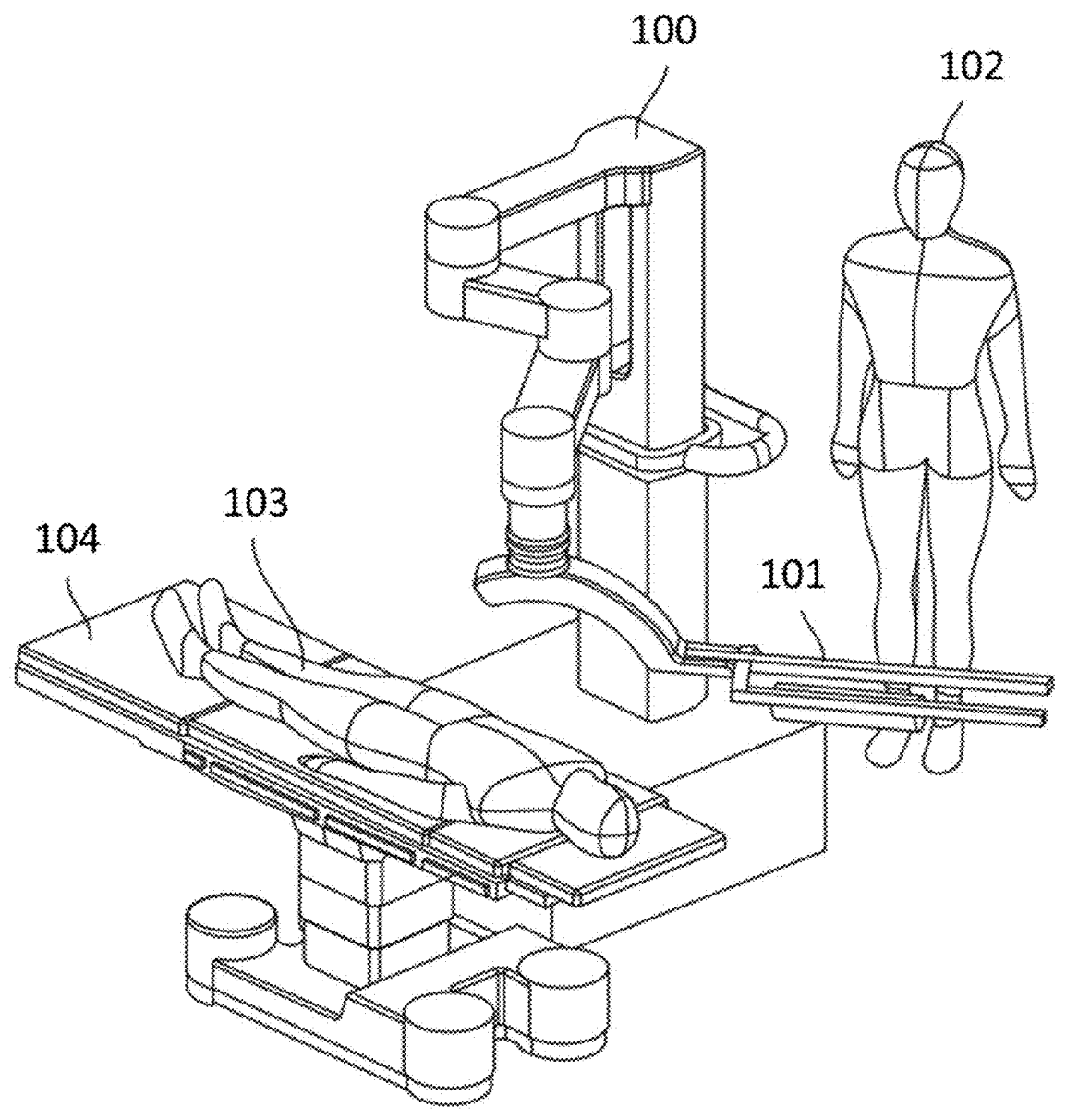
Figure 3:
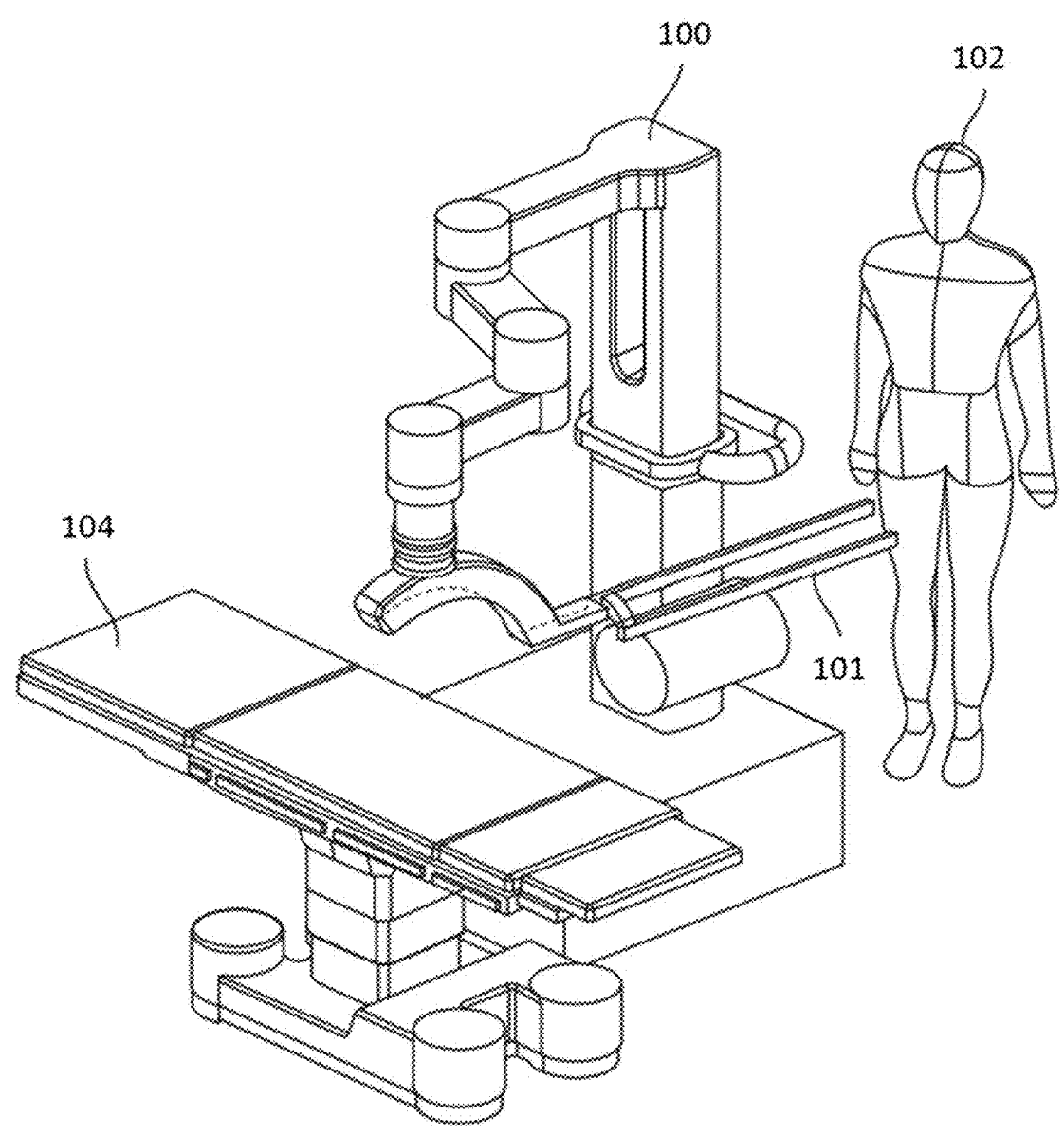

As shown in the sequence of images of FIGS. 1-3, a surgical procedure may be performed by a medical professional 102 (such as a surgeon) on a subject (e.g., patient) 103 with the assistance of a robotic machine 100 having a robotic assembly 101. At least a portion of the robotic assembly 101 may be inserted in a portion of the patient 103. At least a portion of the robotic assembly 101 may remain outside of the patient 103. The portion that may be inserted may include a camera and two robotic arms. The portion that may remain outside of the patient 103 may include motor units, rails, portions of support tubes, control systems, and others. The patient 103 may be positioned on a surface 104, such as an operating table. The robotic assembly 101 may be movable. The robotic assembly 101 may be positioned over an area of a patient. The surgical procedure may include inserting a portion of the robotic assembly 101 into a portion of the patient 103, in some cases, through one or more trocars. The surgical procedure may include a therapeutic procedure, a diagnostic procedure, a prophylactic procedure, a theranostic procedure, or any combination thereof.

A robotic assembly may comprise one or more magnets, such as a magnetic sensing system of a robotic assembly. The magnetic sensing system may be positioned within a portion of the robotic assembly, such as a joint. One or more joints of a robotic assembly may comprise a magnetic sensing system, comprising one or more magnets. A magnetic field of one or more magnets may change as a result of a displacement or movement of a portion of the robotic assembly, such as a joint. A corresponding one or more sensors may be configured to measure the change in the magnetic field. A magnet of the magnetic sensing system may be a ring magnet, a circular magnet, a bar magnet, a horseshoe magnet, a ball magnet, a cylindrical magnet, or any combination thereof. A magnet or portion thereof may be a ceramic magnet. A magnet or portion thereof may comprise neodymium, boron, iron, or any combination thereof. A magnet or portion thereof may comprise neodymium, ferrite, rubber, iron, lodestone, magnetite, or any combination thereof. A magnet or portion thereof may comprise neodymium-iron-boron (NdFeB). A magnet or portion thereof may comprise a magnetic strength from about N33 to N52. A magnet may comprise a magnetic strength of about N35. A magnet may comprise a magnetic strength of about N42. A magnet or portion thereof may comprise a magnetic strength from about Y10 to Y30BH. A magnet or portion thereof may be an isotropic magnet, A magnet or portion thereof may be an anisotropic magnet. A magnet or portion thereof may comprise a rubber magnet. A magnet or portion thereof may comprise ferrite, aluminum-nickel-cobalt (AlNiCo or AN), samarium cobalt (SmCo or SC), neodymium-iron-boron (NdFeB or ND), or any combination thereof. A magnet or portion thereof may comprise an electromagnet.

A robotic assembly may comprise one or more sensors. A magnetic sensing system of a robotic assembly may comprise one or more sensors. The sensors may be positioned within a portion of the robotic assembly, such as a joint. One or more joints of a robotic assembly may comprise a magnetic sensing system, comprising one or more sensors. A sensor may be configured to measure a change in a portion of a magnetic field of one or more magnets that corresponds to a displacement or movement of a portion of the robotic assembly, such as the joint. A sensor may be configured to measure a change in a portion of a magnetic field. A sensor may comprise a search-coil magnetometer, a flux-gate magnetometer, an optically pumped magnetometer, a nuclear-procession magnetometer, a superconducting quantum interference device (SQUID) magnetometer, a Hall-effect sensor, a magnetoresistive magnetometer, a magnetodiode, a magnetotransistor, a fiber-optic magnetometer, a magneto-optical sensor, or any combination thereof.

A robotic assembly may comprise a plurality of joints. At least two joints of the plurality of joints may be of a same type. At least two joints of the plurality of joints may be of a different type. A robotic arm of the robotic assembly may comprise a plurality of joints. A joint may be configured for translational motion, configured for rotary motion, or any combination thereof. A robotic assembly may comprise a joint configured for translational motion, a joint configured for rotary motion, or a combination thereof. A joint may be a linear joint, an orthogonal joint, a rotational joint, a twisting joint, or a revolving joint. A robotic assembly may comprise a linear joint, an orthogonal joint, a rotational joint, a twisting joint, a revolving joint, or any combination thereof. A joint may comprise a hinge joint or a rotary joint. A robotic assembly may comprise a hinge joint, a rotary joint, or a combination thereof.

A robotic assembly may comprise 1, 2, 3, 4, 5, 6, 7, 8, 9, 10, 15, 20 joints or more. A robotic assembly may comprise at least about 2, 3, 4, 5, 6, 7, 8, 9, 10, 15, 20 joints or more. A robotic arm may comprise 1, 2, 3, 4, 5, 6, 7, 8, 9, 10, 15, 20 joints or more. A robotic arm may comprise at least about 2, 3, 4, 5, 6, 7, 8, 9, 10, 15, 20 joints or more. A robotic assembly may comprise one or more hinge joints. A robotic assembly may comprise one or more rotary joints. A robotic arm of a robotic assembly may comprise one or more hinge joints, one or more rotary joints, or a combination thereof. A robotic arm may comprise from about 1 to 10 hinge joints, from about 1 to 10 rotary joints, or a combination thereof. A robotic arm may comprise from about 2 to 15 hinge joints, 2 to 15 rotary joints, or a combination thereof. A portion of a robotic arm may comprise an alternating pattern of hinge joints and rotary joints. A portion of a robotic arm may comprise a repeating pattern of hinge joints or a repeating pattern of rotary joints. A pattern of joints may be configured such that the robotic arm moves with at least 7 degrees of freedom, with at least 8 degrees of freedom, or more.

A robotic assembly may include a robotic arm. A robotic assembly may include more than one robotic arm. At least a portion of the robotic arm may be configured to enter and execute tasks within a body cavity of a subject. A robotic arm may comprise an end effector. The end effector may be coupled to a distal end of the robotic arm. A robotic arm may comprise more than one end effector, such as 2, 3, or more end effectors. An end effector may be coupled and decoupled from a robotic arm. An end effector of a first robotic arm may be a different type as an end effector of a second robotic arm of the robotic assembly. An end effector of a first robotic arm may be a same type as an end effector of a second robotic arm of the robotic assembly. An end effector may comprise a forceps, a needle, a scalpel, a clamp, a scissors, a hook, a retractor, a clamp, a suction tool, a stapler, a cystoscope, a saw (such as a bone saw), an arthroscope, an energy tool (such as an electrocautery tool, an ultrasonic tool, or an endostapler), or any combination thereof.

A robotic assembly may include one or more working ends. A robotic assembly may comprise 1, 2, 3, 4, 5, 6, 7, 8, 9, 10 working ends or more. A robotic assembly may comprise at least 2, 3, 4, 5, 6, 7, 8, 9, 10 working ends or more. A working end may be a portion of a robotic assembly that enters a body cavity. A working end may comprise a camera, a robotic arm comprising an end effector, or other robotic component. A working end may be inserted through a trocar to enter the body cavity. In some cases, 1, 2, 3, 4, 5, 6, 7, 8, 9, 10 working ends or more may be inserted through a trocar. In some cases, at least about 2, 3, 4, 5, 6, 7, 8, 9, 10 working ends may be inserted through a trocar. In some cases, a subset of working ends may be inserted into a body cavity by passing through a first trocar and a second subset of working ends may be inserted into the body cavity by passing through a second trocar. In some cases, a robotic assembly comprises 3 working ends that pass through a single trocar.

A robotic assembly may comprise an elastic element. The elastic element may be configured to be operatively connected to or embedded within a working end of the robotic assembly (such as a working end of a robotic arm or a working end of the camera), a transition element, a support tube, a motor unit or any combination thereof. A working end of the robotic assembly may be operatively coupled to a corresponding elastic element. Each working end of the robotic assembly may be operative coupled to a corresponding elastic element. The elastic element may cause an outward bias of working ends inserted into a trocar such that a connect support tube is driven radially outward to a position adjacent to an inner wall of the trocar. The elastic element may comprise a spring or elastic band or rubber band. A spring may comprise a compression spring, an extension spring, a torsion spring, a constant force spring, or any combination thereof. A spring may comprise a flat spring, a spiral spring, a helical spring, a disc spring, a tubular spring, a membrane, an aneroid box, a bellow, or any combination thereof.

A robotic assembly or portion thereof as described herein may comprise one or more coatings. For example, electrical components of a robotic arm of the robotic assembly may be coated with a coating. The coating may comprise a conformal coating. A coating or portion thereof may be polymer-based, such as an amorphous fluoropolymer. A coating or portion thereof may comprise an acrylic resin, a silicone resin, a urethane resin, an epoxy resin, a parylene, a silicone, or any combination thereof. A coating or portion thereof may comprise a nano-coating, a thin film coating, or a combination thereof.

Range of Movement

Previous generations of surgical robotics arms may have no more than seven degrees of freedom, including the end effector. Many surgical robots may operate with fewer than seven degrees of freedom. Seven degrees of freedom, in most instances, may allow the user (e.g., surgeon) to both position and orient the end effector of the robot/surgical tool in a range of positions or orientations within a work space (seven degrees of freedom=x, y, z, yaw, pitch, roll, end effector open/close). However, there may be only one permissible position for each joint of the robot for each position and orientation of the end effector. For example, the elbow of the robot may only be in one place for a given position and orientation of the end effector.

By incorporating eight or nine degrees of freedom (DOF), the disclosed robotic arm is able to execute certain approach paths not available for robotic arms with only seven degrees of freedom (e.g., reaching up toward the ceiling of the abdomen (ventral wall) and operate). In some embodiments, the robot can reach around tissue and approach any organ from the back, just like a human can pick up a coffee mug from the back without rotating the mug. This is impossible with currently available robotic surgical systems for minimally invasive surgical operation. According to some embodiments, the disclosed robotic arm enables a surgeon to choose a more ideal approach path and approach any tissue from almost any angle.

A robotic assembly, such as a surgical robotic assembly, may comprise a robotic arm. In some cases, a robotic arm comprises a plurality of joints. The plurality of joints can be arranged sequentially from an origin of the robotic arm to an end effector of the robotic arm. The plurality of joints may form one or more sections, such as a plurality of sections. In some cases, a first section of the robotic arm may comprise the origin, such as a shoulder of the robotic arm. A second section of the robotic arm may comprise a robotic elbow joint. A third section of the robotic arm may comprise an end effector (such as a surgical tool). The robotic arm may comprise a joint positioned within the first section (such as a hinge joint) and a joint positioned with the third section (such as a hinge joint) to provide movement of at least a portion of the second section independently from a movement of the origin or the end effector of the robotic arm. In some cases, a combination of a joint positioned within the first section and a joint positioned within the third section permit movement of at least a portion of the second section independent from movement of the origin and the end effector. The robotic elbow joint may be a hinge joint, to mimic a human elbow. The plurality of joints of the robotic arm may comprise any combination of different types of joints, such as a hinge joint, a rotary joint, or a combination thereof. The plurality of joints of the robotic arm may comprise at least 3 hinge joints, at least 3 rotary joints, or a combination thereof. Positioning of the plurality of joints to form the robotic arm, such as an arrangement of joints or a pattern of joints. A portion of the robotic arm may comprise a section of joints positioned with an alternating pattern of a hinge joint and a rotary joint. An end effector may be coupled to a hinge joint. The positioning of the plurality of joints may permit a range of movement of the robotic arm. The range of movement of the robotic arm may comprise at least 7 degrees of freedom, at least 8 degrees of freedom, or more. The range of movement of the robotic arm may be substantially similar to a human arm. A size of the robotic arm may be configured for placement through a trocar and into a body cavity.

A hinge joint may be configured for rotational motion about an axis substantially perpendicular to a lengthwise axis of the robotic arm. A hinge joint may be configured for movement along a singular plane. A rotary joint may be configured for a parallel motion about an axis substantially lengthwise of the robotic arm.

Movement of one or more joints of the robotic arm may be performed by a motor unit, which may be disposed outside of the robotic arm. A joint of the plurality of joints may be operatively coupled to a corresponding motor unit. Each joint of the plurality of joints may be operatively coupled to a corresponding motor unit. Displacement of one or more of the plurality of joints may be measured by a magnetic sensing system. The robotic arm may comprise a magnetic sensing system. A joint of the plurality of joints may comprise a corresponding motor unit. Each joint of the plurality of joints may comprise a magnetic sensing system. A magnetic sensing system may be positioned within a portion of a joint of the robotic arm.

Figure 4:
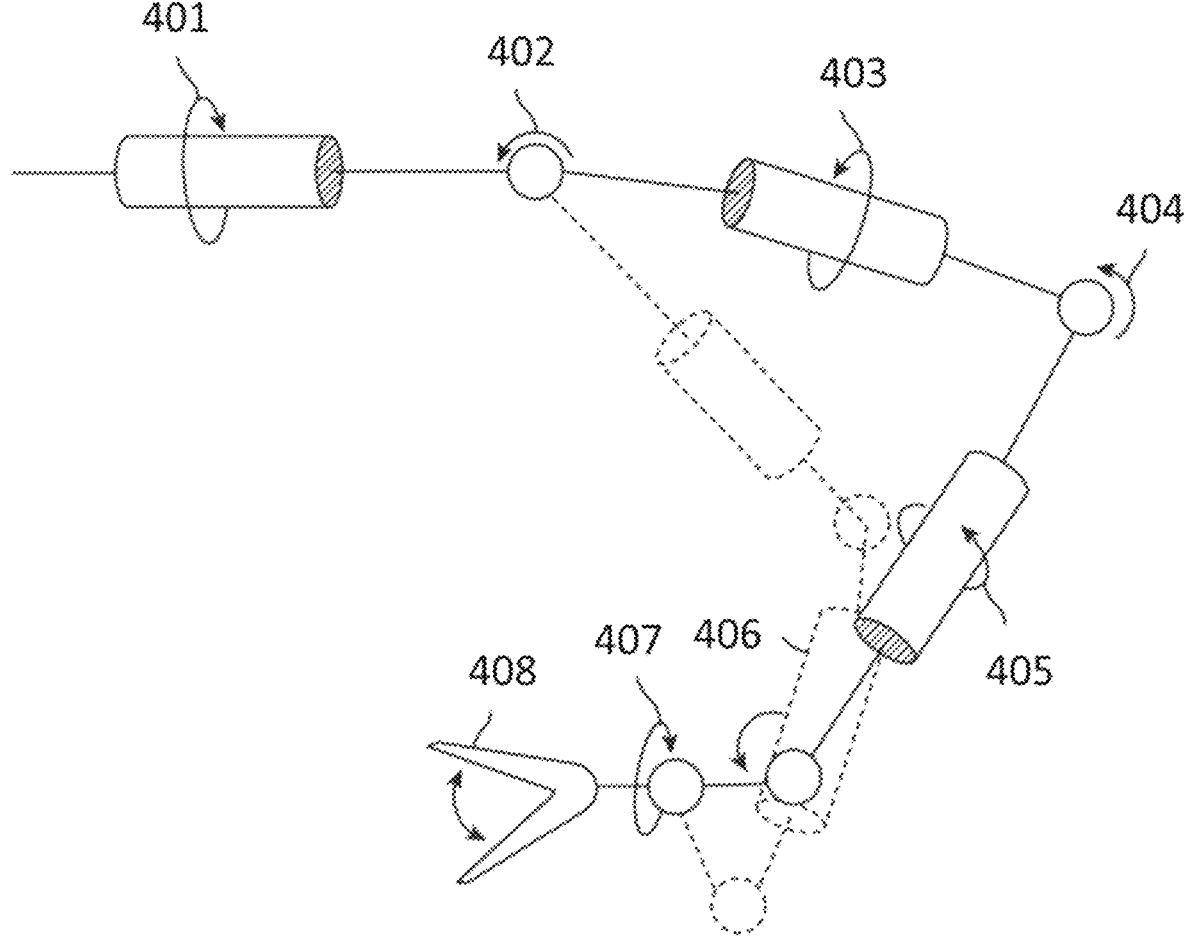
FIG. 4 illustrates an example of a robotic arm comprising a plurality of joints.

FIG. 4 illustrates a surgical robot. The arm of the robot has the same configuration as a human arm. That is, the robot can drop its elbow and operate on the ceiling of the abdomen while keeping the end effector in the same position and orientation. As shown in FIG. 4, the configuration of the robot is (from the shoulder and in order): a first rotary joint 401, a first hinge joint 402, a second rotary joint 403, a second hinge joint 404, a third rotary joint 405, a third hinge joint 406, a fourth hinge joint 407, and an end effector 408. In some embodiments, the hinge joints 402, 404, 406, and 407 are defined as having rotational motion in an axis perpendicular to the lengthwise axis of the arm. In some embodiments, the rotary joints 401, 403, and 405 are defined as having motion parallel to the lengthwise axis of the arm.

According to certain embodiments, a range of motions based on these eight degrees of freedom can be achieved entirely within the abdominal cavity or bodily cavity in a human-like orientation. In some embodiments, a range of motions can be achieved with any number of degrees of freedom outside of the abdominal cavity. In some instances, a motion based on four degrees of freedom can be achieved outside of the incision site.

According to certain embodiments, various suitable robotic actuators or other surgical robotic technologies including flexible robotics can be used with the disclosed system. According to some embodiments, the surgical apparatus system of FIG. 1 incorporates specialized actuators disclosed in U.S. Pat. No. 10,285,765 B2 titled Virtual Reality Surgical Device, and/or in United States Patent Application Publication 2019/0142531 A1 titled Virtual Reality Wrist Assembly, both references are attached in the appendix and are herein incorporated in their entirety.

Referring back to FIG. 4, the solid and dotted lines depict two exemplary configurations/positions of the robot arm. Notably, the elbow (at the second hinge joint 404) can move into various positions without moving/adjusting the end effector or the origin of the arm (e.g., shoulder).

Magnetic Sensing Systems

A robotic assembly may comprise a magnetic sensing system, such as a magnetic sensing system for a robotic joint (such as a robotic joint of a cable-drive robotic arm). A robotic joint may be operatively coupled to a corresponding magnetic sensing system. A robotic joint may comprise a corresponding magnetic sensing system. The magnetic sensing system may be configured for sensing displacement or movement of the robotic joint.

A magnetic sensing system may comprise a magnet and a sensor. The sensor may be configured to sense a change in at least a portion of a magnetic field of the magnet. The magnetic sensing system may comprise a plurality of magnets and a plurality of sensors. A sensor may be configured to measure a change in at least a portion of a magnetic field of at least a portion of the plurality of magnets.

One or more magnets of a magnetic sensing system may be positioned in an arrangement. The arrangement of magnets may form a magnetic field. One or more sensors of a magnetic sensing system may be positioned in an arrangement. The arrangement of sensors may individually measure at least a portion of the magnetic field produced by the one or more magnets. An arrangement of sensors and magnets may be configured to optimize (i) space for a plurality of components (such as cables) to be housed or pass through a joint (such as a cable-driven robotic arm), (ii) range of motion or movement of the joint, (iii) accuracy of a measurement of the magnetic sensing system, or (iv) any combination thereof.

An arrangement may include one or more magnets. An arrangement may include at least 2 magnets. An arrangement may include at least 4 magnets. Two or more magnets may be arranged substantially in a column. Two or more magnets may be arranged substantially within a single plane, such as 4 magnets arranged substantially within a single plane. An arrangement of magnets may comprise an array of magnets, such as 2×2 magnets, 2×3 magnets, 2×4 magnets, 3×4 magnets, 4×4 magnets, or others.

Magnets each having a N pole and a S pole may be arranged relative to each other in a number of different ways. Two magnets (such as magnets each arranged substantially in a different column) may be oriented with opposing dipoles to one another such that the first magnet is oriented N-S relative to the second magnet and the second magnet is oriented S-N relative to the first magnet. Magnets of a first column may be positioned so that their dipoles are oriented in an alternating orientation relative to dipoles of a second column, such as a first column oriented N-S, N-S and a second column oriented S-N, S-N. A magnet having a dipole of N-S may be positioned diagonally, obliquely, or transversely from a magnet with a dipole of S-N. A S pole of a magnet may directly face a N pole of a second magnet. A side of a magnet moving from a N pole to a S pole may directly face a side of a second magnet positioned to move from a S pole to a N pole.

Arrangement of the one or more magnets may form a magnetic field. A change in at least a portion of the magnetic field may be measured by one or more sensors. The magnetic field may comprise an orthogonal field component, a parallel field component, a non-parallel field component, or any combination thereof.

Magnets may be arranged within sections of the joint. For example, a joint comprising two magnets may have a first magnet positioned in a first half of the joint and a second magnet positioned in a second half of the joint. A joint comprising four magnets may have a first magnet positioned in a first quadrant of the joint, a second magnet positioned within a second quadrant of the joint, a third magnet positioned within a third quadrant of the joint, and a fourth magnet positioned within a fourth quadrant of the joint. This positioning of multiple magnets within subsections of the joint has be implemented with about 2, 3, 4, 5, 6, 7, 8, 9, 10 magnets or more within a single joint.

One or more sensors may form an arrangement of sensors substantially along a single plane. The plane of sensors may be positioned substantially perpendicular to one or more magnets or an arrangement of magnets. The plane of sensors may be positioned substantially parallel to one or more magnets or an arrangement of magnets. One or more sensors may form an arrangement of sensors along more than one plane. An arrangement of sensors may comprise an array of sensors, such as 2×2 sensors, 2×3 sensors, 2×4 sensors, 3×4 sensors, 4×4 sensors, or others.

A plane of sensors (such as positioned substantially perpendicular to an arrangement of magnets) may be positioned between two or more magnets. A plane of sensors may be positioned outside of the arrangement of magnets. A plane of sensors may be positioned between a first magnet of a column and a second magnet of the column. A plane of sensors may be positioned between a first magnet of a first column and a second magnet of a second column.

One or more magnets of the magnetic sensing system may be positioned substantially to a peripheral edge of the robotic joint. One or more sensors may be positioned substantially distal to a central location of the robotic joint. One or more sensors of the magnetic sensing system may be positioned substantially to a peripheral edge of the robotic joint. One or more magnets may be positioned substantially distal to a central location of the robotic joint.

Arrangement of the magnet and sensor of the magnetic sensing system may provide measurement of robotic joint displacement with a higher resolution as compared to a comparable robotic joint lacking the arrangement. The higher resolution may be about 1.1×. 1.2×, 1.3×, 1.4×, 1.5×, 1.6×, 1.7×, 1.8×, 1.9×, 2.0× greater or more.

Arrangement of the magnet and sensor of the magnetic sensing system may provide measurement of robotic joint displacement with a higher accuracy as compared to a comparable robotic joint lacking the arrangement. The accuracy of measurement may be at least about 70%, 80%, 85%, 90%, 95%, 96%, 97%, 98%, 99% or more accurate.

The virtual diametric magnet system disclosed herein may be designed to be incorporated in and/or utilized with the robotic arms as disclosed in U.S. Pat. No. 10,285,765 B2 titled Virtual Reality Surgical Device, which is incorporated by reference herein in its entirety, and/or the wrist assemblies disclosed in International Patent Publication No. WO2019094896A1 (International Patent Application No. PCT/US2018/60656, titled Virtual Reality Wrist Assembly), which is incorporated by reference herein in its entirety. In some embodiments, the virtual diametric magnet system can also be implemented and utilized by other existing and future surgical robotic systems or devices.

As used herein, a magnet at least includes an object or collection of objects capable of generating a magnetic field, including but not limited to Neodymium, Iron, and other formulations of permanent magnets, electromagnets, and/or any other objects capable of generating magnetic fields.

As used herein, a sensor includes an object or collection of objects capable of measuring magnetic field strength, or capable of measuring some quantity from which magnetic field strength can be derived, including but not limited to, integrated circuits (ICs), MEMS systems, discrete electronic components, mechanical transducers, purely mechanical computational machines, and/or any other suitable objects usable to measure or transduce magnetic fields.

As used herein, a joint includes an object or collection of objects capable of relative displacement, either translational or angular.

As used herein, a sensor array includes a single sensor, or a collection of sensors, positioned relative to a magnet and each other such that the sensor is positioned to measure one or more components of the magnetic field that vary with joint displacement.

Electrical Communication

In a complex multi-degree of freedom system, having a continuous electrical communication component is not always feasible from an assembly or manufacturing standpoint. In some instances, to deal with the spatial constraints, multiple electrical communication components are utilized with the electrical communication components operably coupling to each other. Each communication component is designed such that it can be placed in a device whether or not the device is already assembled. This allows for ease of repair in the event of a failure or during repurposing after an operation. As the number of degrees of freedom increases, the amount of data increases as well, as each joint is independently sensed. Microcontrollers along the electrical communication components allow the data gathered at each sensor to be processed and retransmitted in such a way that the number of electrical conductors per component can be reduced. This allows for many sensors to be placed in a chain of electrical communication components with fewer number of conductors. As a result, the width or thickness of the electrical communication components may not be too large.

According to some embodiments, the systems disclosed herein are used to route electrical communication components through a nine degrees of freedom surgical robotic device that has position sensing elements to provide a closed loop control of each joint of the robotic device. The systems are configured to ensure the control input from the control system is achieved accurately and precisely. In some embodiments, different electrical communication components may be utilized, including but not limited to flexible printed circuit boards ("FPCB"), fiber optic cables and/or other communication elements capable of transmitting and receiving electrical signals.

Various methods for routing electrical communication components through different types of robotic joints and actuators are disclosed herein. Some examples of robotic joints are described in the aforementioned patent and patent application, including but not limited to hinge joints/actuators and rotary joints/actuators. According to some embodiments, the disclosed routing methods allow electrical signals and communications such as Hall-effect sensor readings and camera sensor readings to pass from a distal portion of a device to a control system or vice versa. In some embodiments, the electrical communication components have one or more moving sections, designed to move with respect to the motion of one or more robotic joints. To avoid fatiguing the electrical communication components, as they pass through each joint, the moving sections of the electrical communication components are designed to have as large of a radius of curvature as possible and to have any bending occur over multiple regions rather than over a single point. In some embodiments, the moving sections are constructed as coils of flexible circuits, wrapped around the axis of the joint or about another point. In some embodiments, the moving sections can be folded in half in a linear motion, where the two ends of the electronic communication component are fixed to two different bodies, and the folding (or bending) portions move relative to the fixed ends. In some embodiments, the moving sections are constructed as coils as discussed above with moving sections which can be folded in half. These disclosed systems/methods facilitate the transmission data out of a dynamic system without impacting the rest of system.

A robotic arm of a robotic system may comprise one or more joints. A joint of the robotic arm may comprise at least a portion of an electrical communication component. The electrical communication component may comprise a portion of which passes through the joint and operatively ends to two end points, such as operatively connecting an end effector with an origin of the robotic arm or operatively connecting an end effector (such as a surgical tool) with a control system. The electrical communication component may be configured to transmit one or more electrical signals to or from a portion of the robotic arm. The electrical communication component may be configured to transmit one or more electrical signals to or from a joint of the robotic arm. The portion of the electrical communication component may move during actuation or movement of the joint to permit range of motion of the joint, to prevent substantially bending, folding or damage to the portion, or a combination thereof. An arrangement of the portion to permit movement of the portion as the joint moves may preserve range of motion of the joint and protect the portion against damage to the electrical components from bending or distortion. During movement of a portion of the joint, an arrangement of a portion of the electrical communication component may be configured to substantially maintain a radius of curvature, such as by wrapping or forming a moving bend. An arrangement may comprise a wrapping arrangement, a moving bend arrangement or others. Additional elements that may assist in preventing damage to a portion of the electrical communication component may include incorporating a stopping element into a portion of the robotic arm to limit a range of motion of at least a portion of the robotic arm. A stopping element may at least partially limit an overextension or over-compression of a portion of the electrical communication component. Incorporation of a coating or a film that covers at least a portion of the electrical communication component may prevent damage to at least a portion of the electrical communication component. The coating or film may comprise a lubricant.

At least a portion of the electrical communication component within the joint may be wrapped around an axis of the joint (such as a rotary joint), to form at least a partial helical wrap or at least a partial coil. The number of wraps may be positioned within a housing of a joint. The number of wraps may be positioned outside of a shaft of a joint. The number of wraps may be positioned between an inner wall of a housing and an outer wall of a shaft of the joint. The number of wraps of the portion may vary as a joint moves. The number of wraps of the portion may vary proportionally to a range of motion of the joint. At a first range of motion of a joint, the number of wraps may be maximized. At a second range of motion of the joint, the number of wraps may be minimized. The number of wraps may be tightly wrapped around an axis of the joint (such as the shaft). The number of wraps may be expanded outwardly toward in inner wall of a housing and loosely wrapped around the shaft. During movement of the joint, the wrapping of the electrical component may be maintained with the number of wrapping varying. Joints having a wrapping of the electrical component may be a rotary joint or a hinge joint. Joints having the wrapping may be a rotary joint.

At least a portion of the electrical communication component may be extended within the joint (such as a hinge joint) to form a moving bend. During actuation of the joint, at least a portion of the moving bend may move. During actuation of the joint, at least a portion of the moving bend may move proportionally to a range of motion of the joint. Joints having a moving bend may be a rotary joint or a hinge joint. Joints having a moving bend may be a hinge joint.

A moving bend may be positioned outside of the joint. The moving bend may be positioned within a portion of the joint—such as a housing. The moving bend may be positioned within a channel of the housing. At least a portion of the channel may be physically separated from the joint. The channel may be positioned outside of a central axis of the joint. During movement of the joint, the amount of the moving bend positioned within the channel may vary. The amount of the moving bend positioned within the channel may vary proportionally to a range of movement of the joint. For example, at a first range of motion of the joint, a minimum amount of the moving bend may be positioned within the channel. At a second range of motion of the joint, a maximum amount of the moving bend may be positioned within the channel. The moving bend may fold upon itself and extend to accommodate different amounts of the moving bend within the channel.

Camera and Visualization Systems

Figure 5:
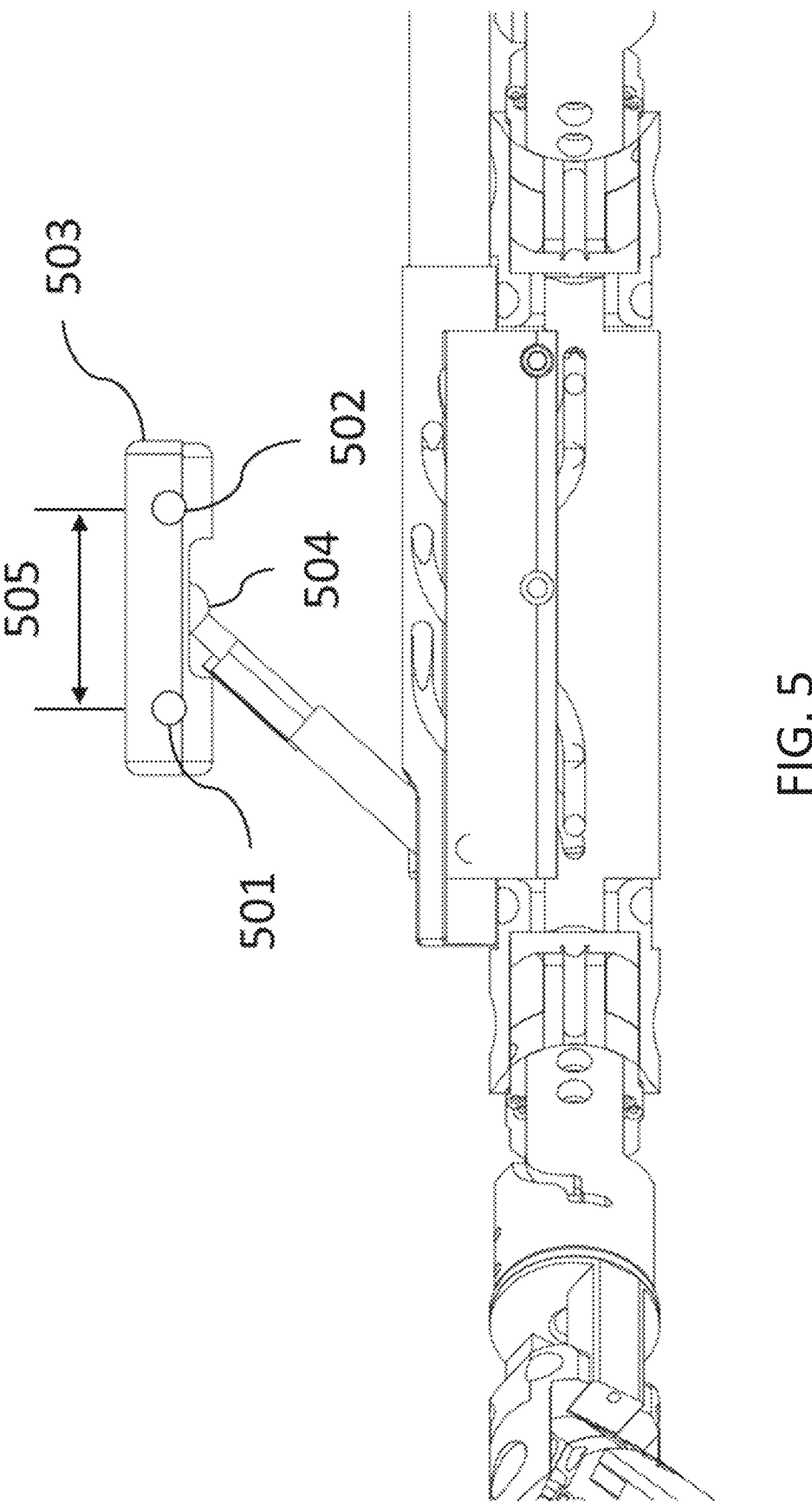
FIG. 5 illustrates an example of an isometric front view of a camera.

The camera system shown in FIG. 5 comprises a first camera 501 and a second camera 502 disposed within, adjacent to, or on top of a camera body 503. The camera body pivots with two degrees of freedom by actuation of the ball joint 504. This motion in two degrees of freedom forms the camera's pan system and tilt system (e.g., yaw and pitch). The pan system adjusts the camera's view in in the pan axis while the tilt system adjusts the camera's view in the tilt axis. In alternative embodiments, the ball joint is replaced with two hinge joints or a rotary joint and a hinge joint. In yet another embodiment, a rotary joint rotates the camera body about the vertical axis while tilt motion is provided by digitally adjusting the camera view. Position sensors accurately measure the position of each joint that moves the camera body. Position sensors may include any of Hall-effect sensors, optical encoders, resistive position sensors, or any other standard means of measuring position.

In another embodiment, cameras move within the camera body such that one or both of pan and tilt adjustments are provided by movement of the cameras within the camera body. This adjustment may be used in conjunction with camera body movement, or instead of camera body movement. Cameras may move together, or separately. Cameras may move by motor actuation, cable actuation, or any other standard actuation means. Alternatively, cameras may rotate freely in two degrees of freedom and move under the direction of a magnetic field created by magnetic coils surrounding the camera.

In some embodiments, both pan and tilt motion are provided by digital pan and tilt adjustment. Digital adjustment is provided by cropping the digital camera image. The cropped image adjusts automatically such that as a pan or tilt movement is desired, the portion of the image displayed to the user changes, thus creating the illusion of camera movement. In another embodiment, a combination of digital and mechanical adjustment are used such that digital pan and tilt adjustment makes minor and rapid adjustments while mechanical pan and tilt adjustment allows for large pan and tilt movements.

In another embodiment, the camera assembly is inserted into the abdomen as a separate unit from the rest of the device. This separate camera assembly may removably couple with the device once inside of the abdominal cavity, or it may serve as a stand-alone unit.

In some embodiments, the cameras have wide-angle lenses allowing for a wide visualization of the operating field. In other embodiments, the cameras have aspherical lenses allowing for a wide vertical view with a narrow horizontal view. Distortion is removed with digital adjustment. This wide vertical view allows for a tilt motion to be provided solely using digital technique. In yet another embodiment, the camera body 503 comprises a plurality of camera devices further increasing the field of view. Camera views are digitally interlaced to form one large image with a panoramic view. Standard digital technique known in the field is used to interlace images. In another embodiment, the camera body additionally comprises other sensors sensing any of pressure, capacitance, temperature, infrared, ultraviolet, or any other sensor device.

In one embodiment, the camera body 503 further comprises an array of LEDs positioned between one camera 501 and the second camera 502, or one array of LEDs positioned on either side of the cameras. Notably, the specific location of the LEDs on the camera body is not limited. These LEDs serve to illuminate the operating field. These LEDs are powered via wires fed to the outside of the body. Heat from the LEDs is dissipated within the camera body. In some embodiments, a small amount of sterile saline or other biocompatible fluid may flow through the camera body to cool the camera body. Other embodiments further comprise a temperature sensor to ensure the camera body remains within a safe temperature range. In another embodiment LEDs are placed within other bodies of the device providing for different angles of lighting as well as larger heat-sink bodies.

It is thought that the abdomen may also be illuminated via fiber optics or another lighting source. Fiber optics may be fed into the body with actuation cables, or through another incision. In one embodiment, optical fibers are threaded into the abdomen through very small tubes such as 21-gauge angiocatheters. Fibers could mate with the device inside of the abdomen, or could serve to provide illumination without mating with the device. Such an illumination system may provide for increased lighting with reduced heat, but at the cost of increased complexity of the overall system.

The camera body is inserted with its field of view perpendicular to the direction of insertion through the trocar. This allows placement of cameras on or in the camera body 503 (FIG. 5) such that the inter-camera distance 505 exceeds the size of the incision through which the device is inserted. With increased inter-camera distance, the camera system has increased ability to visualize parallax and allow a user to perceive depth. The inter-camera distance is chosen to maintain a natural and human-like system such that $$\frac{\text{length of human arm}}{\text{human interpupillary distance}}$$

approximately equals $$\frac{\text{length of robotic arm}}{\text{inter}-\text{camera distance}}.$$

Human Interaction with Device

The apparatus disclosed provides numerous advantages for surgeons, as it allows a surgeon to interact with the in vivo robotic device as if the device were the surgeon's arms and hands. This allows a surgeon to perform very difficult and delicate procedures in close quarters, while allowing said surgeon to maintain the natural motions to which he or she is accustomed when performing a procedure. The apparatus disclosed allows a surgeon to perform an operation in the manner and form in which he or she is accustomed, while being able to access areas of the body that may not otherwise be accessible using other robotic devices. Furthermore, the apparatus in some embodiments, increases the surgeon efficiency during a procedure due to the surgeon ability to maintain a natural and intuitive human-machine interface (HMI), while being immersed in virtual reality. This helps to reduce the operation time, and thus allowing a patient to commence their recovery sooner. Likewise, the increase in efficiency, helps a surgeon concentrate on performing a procedure, thus increasing a surgeon's work flow and improving his or her productivity. In some embodiments, the surgeon interacts with the human-machine interface (HMI) via virtual reality using a wearable device. In some embodiments, the surgeon interacts with the human-machine interface (HMI) via virtual reality in conjunction with one or more hand controllers.

A HMI was designed to provide improved utilization of the human-like robotic device and natural visualization system. One embodiment allows the surgeon to control the device with movement of his or her own arms. The surgeon wears a series of elastic bands; each band fastens a sensor to the surgeon's arms. In the one embodiment, this sensor is an MPU-6050 sensor. The MPU-6050 includes a MEMS gyroscope, accelerometer, and digital motion processor to compute the orientation of the sensor.

Figure 6:
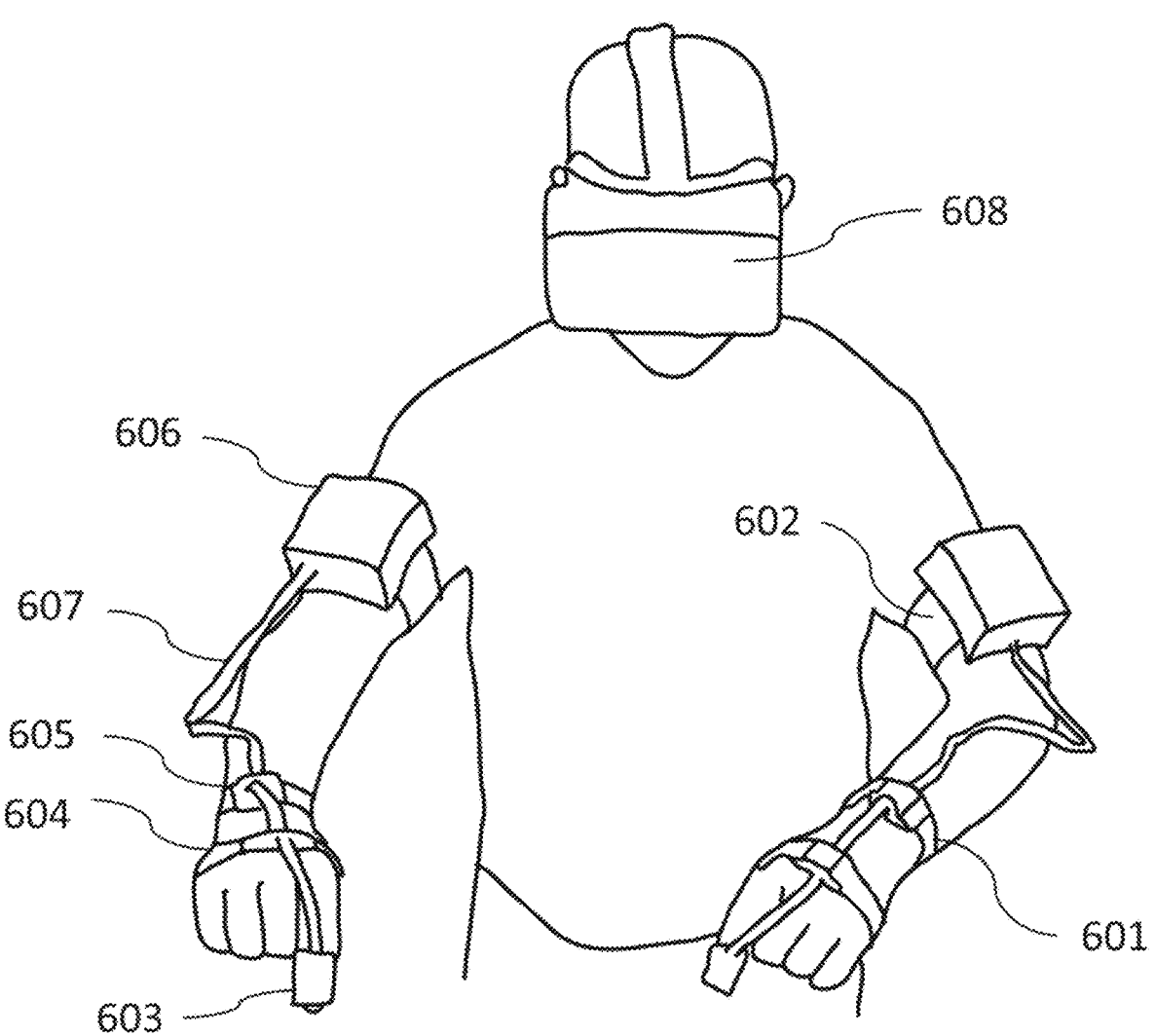
FIG. 6 is an example diagram showing placement of microelectromechanical system (MEMS) sensors on a user with the user wearing a virtual reality headset.

Referring to FIG. 6, in one embodiment, the surgeon wears eight elastic bands 601 and 602. These bands fasten eight MPU-6050 sensors to the surgeon's arms as shown in FIG. 6. One band is placed on each of the right and left index finger 603, hand dorsum 604, distal dorsal forearm 605, and distal dorsal upper arm 606. The enclosure containing each upper arm sensor additionally contains a microcontroller, battery, and Bluetooth module. Data from distal sensors is collected using I2C protocol along wires 607 and transmitted over Bluetooth to a central computer.

With data from the eight MPU-6050 sensors, the central computer is able to compute the position and orientation of each portion of the surgeon's arm. Future solutions include tracking of the surgeon's torso or any other body part. Additionally, an alternate embodiment includes the addition of a MEMS magnetometer with each accelerometer, gyroscope, and motion processor unit. MEMS chips such as the MPU-9250 offer all of the above in a single package. The addition of a magnetometer is standard practice in the field as magnetic heading allows for reduction in sensor drift about the vertical axis. Alternate embodiments also include sensors placed in surgical material such as gloves, surgical scrubs, or a surgical gown. These sensors may be reusable or disposable.

Yet another embodiment includes the addition of sensors to track the position of the surgeon's arms and body. Such sensors, similar to the sensors in the Xbox Kinect® allow tracking of the absolute position of the surgeon's arms and tracking of the arms positions relative to each other. In some embodiments, these additional sensors are worn on the surgeon's body. In other embodiments, sensors are positioned at fixed locations in the room.

With the ability the track the surgeon's arms, a control loop within a central computer drives the servomotors controlling the human-like robotic arms of the device. This can be seen in the block diagram of FIG. 7. Arms are controlled to follow the scaled-down movement of the surgeon's arms. The robotic elbow follows position and orientation of the human elbow. The robotic wrist follows position and orientation of the human wrist. Surgical end-effectors follow the movement of the surgeon's index finger as the surgeon pinches their index finger and thumb together.

While the device's arms follow movement of the surgeon's arms, the device's shoulders are fixed in position. In one embodiment, the position and orientation of the surgeon's torso is subtracted from the position and orientation of the surgeon's arms. This subtraction allows the surgeon the move his or her torso without the arms moving. Alternate embodiments include a chair with pads to encourage the surgeon to keep his or her shoulders in fixed in space. By preventing the surgeon from moving his or her shoulders, the surgeon avoids making movements that the device is unable to replicate, thus increasing the natural feel of the device.

In some embodiments, the surgeon wears a virtual-reality head-mounted display 608 (FIG. 6) in order to provide improved visualization of the device. Head-mounted displays provide the user with a head-mounted display, lenses to allow focused view of the display, and a sensor system to provide position and orientation tracking of the display. Position and orientation sensor systems may include accelerometers, gyroscopes, magnetometers, motion processors, infrared tracking, computer vision, any other method of tracking at least one of position and orientation, or any combination thereof. With many displays emerging on the market, it is important to choose a suitable display for the disclosed system. Display features may result in improved device function for our system include increased flied of view, decreased latency, decreased persistence, increased resolution, decreased weight, increased comfort, and improved display position and orientation tracking. In some embodiments, the display comprises a 2-D display and/or a 3-D display.

Figure 7:
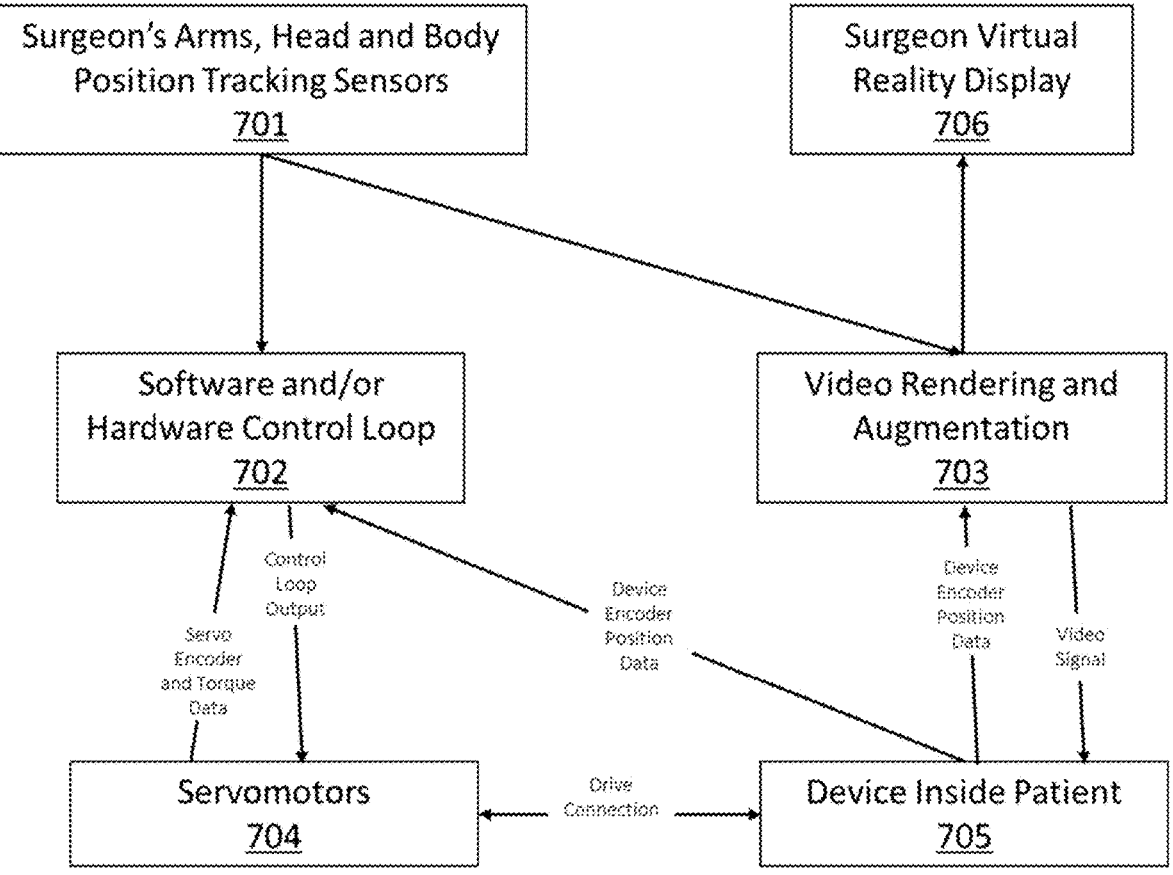
FIG. 7 is an example block diagram of an embodiment of the virtual reality robotic system.

With a head-mounted display, a computer processes video collected from the device's visualization system as seen in the block diagram of FIG. 7. In one embodiment, video from both first and second camera 501 and 502 (FIG. 5) is collected and processed as described later on in this section. Processed video from one camera 501 is displayed to the surgeon's right eye. Similarly, processed video from one camera 502 is displayed to the surgeon's left eye. The combination of left and right eye view from separate cameras spaced apart in the abdominal cavity provides the surgeon with stereoscopic view.

To maintain a full virtual reality experience, a sensor system tracks the position and orientation of the surgeon's head mounted display. This sensor system relays data to a central computer in real time. The central computer adjusts the pan and tilt of the device's camera system as quickly as possible to follow the movement of the user's head. As it is difficult to adjust the pan and tilt of the camera fast enough such that the surgeon cannot perceive a delay, software adjusts the camera views slightly to compensate for any difference between the camera position and the surgeon's head position.

While some embodiments provide only visual feedback to the surgeon, alternative embodiments provide numerous additional feedback systems. In one embodiment, the surgeon holds a device to provide haptic feedback. Such a device could be as simple as a small servomotor connected to two members. When the surgeon squeezes between the members, the servomotor resists the movement. With a servomotor providing haptic feedback as well as with position and force sensing in the robotic grasper, standard force control algorithms may be used to enable the surgeon to "feel" the force exerted by the grasper.

In an alternate embodiment, the surgeon is provided with an exoskeleton-like device to wear on each of his or her arms. Such a device may contain a servo for each actuator of the robotic arms and may allow the surgeon to experience haptic feedback for each robotic actuator. In yet another embodiment the surgeon interacts with the device using standard haptic interaction devices known on the market today.

In one embodiment, motion from the surgeon's arms is translated into motion of the device's arms with only direct scaling. However, other embodiments may include adjustable scaling of the motion. In one embodiment, motion is further scaled down such that a movement of the surgeon's elbow by 10 degrees results in a similar movement of the device's elbow by 5 degrees. This scaling allows for increased dexterity in exchange for decreased natural feel of the device. Another embodiment includes adjustable scaling wherein the scale factor is linked to the speed of movement. For example, if the surgeon's elbow moves 10 degrees at 10 degrees per second, the device's elbow moves 3 degrees. If the surgeon's elbow moves 10 degrees at 50 degrees per second, the device's elbow moves 15 degrees.

The block diagram of FIG. 7 provides an overall view displaying how the device as a whole collects and uses information. Sensors 701 track the surgeons body motion and relay this information to the central computer. The central computer contains control loops 702 and video rendering and augmentation software and hardware 703. Information about the surgeon's arm and body locations are used to calculate intended robotic actuator positions. Control loops continue to calculate power outputs to servomotors 704 using desired robotic actuator positions combined with process values from servomotor encoders, servomotor torque, device encoders, and any other relevant systems. These control loops may use standard tuned proportional integral derivative "PID" control to determine power output to servomotors. Alternatively, custom control loops may be used. Servomotors connect with the device 705 inside of the patient as described herein.

The device inside of the patient collects video signals from camera systems and transmit these signals to the central computer's video rendering and augmentation system 703. This system combines information about the cameras' positions and orientations, the video signals, and the surgeon's head position and orientation. With this information, the video rendering and augmentation system creates a video signal and transmits this signal to the surgeon's virtual reality display 706. It should be noted that this block diagram generally describes the device, alternative embodiments have additional sensors and elements as well as additional connections between block diagram components to allow for more complex processing and use of data within the system.

Reality Augmentation

To further enhance the surgeon's operating capability, reality may be augmented to provide increased information to the surgeon. This augmentation of reality serves to further the surgeon's ability to operate by adding to the virtual reality experience. For example, in one embodiment, the device's cameras have a zoom function. For the surgeon to use this zoom function during an operation may be unnatural, as the surgeon's own eyes are unable to zoom on command. However, using animation, a surgeon may choose a magnifying glass or loupe, and bring the glass in front of his or her virtual eyes during use. This augmented reality allows the surgeon to feel as if he or she caused the increase in zoom, thus maintaining the natural virtual reality connection between surgeon and device.

In another embodiment, the surgeon is able to place augmented reality elements within the patient's abdomen. For example, to view a patient's radiographic scans, a surgeon may choose to place a virtual computer monitor within the patient's abdominal cavity (likely in an area outside the field of operation). This virtual reality monitor allows the surgeon to flip through images without leaving the virtual reality of the operation.

In another embodiment, a computer tracks the position of the robotic arms within the surgeon's field of view. If the surgeon exerts excessive force, the computer augments the color of the robotic arms to appear red within the surgeons view. Similarly, the robotic arms or surgical end-effector may be set to change color when the surgeon enables cautery on a cautery instrument.

Computer Systems

Figure 8:
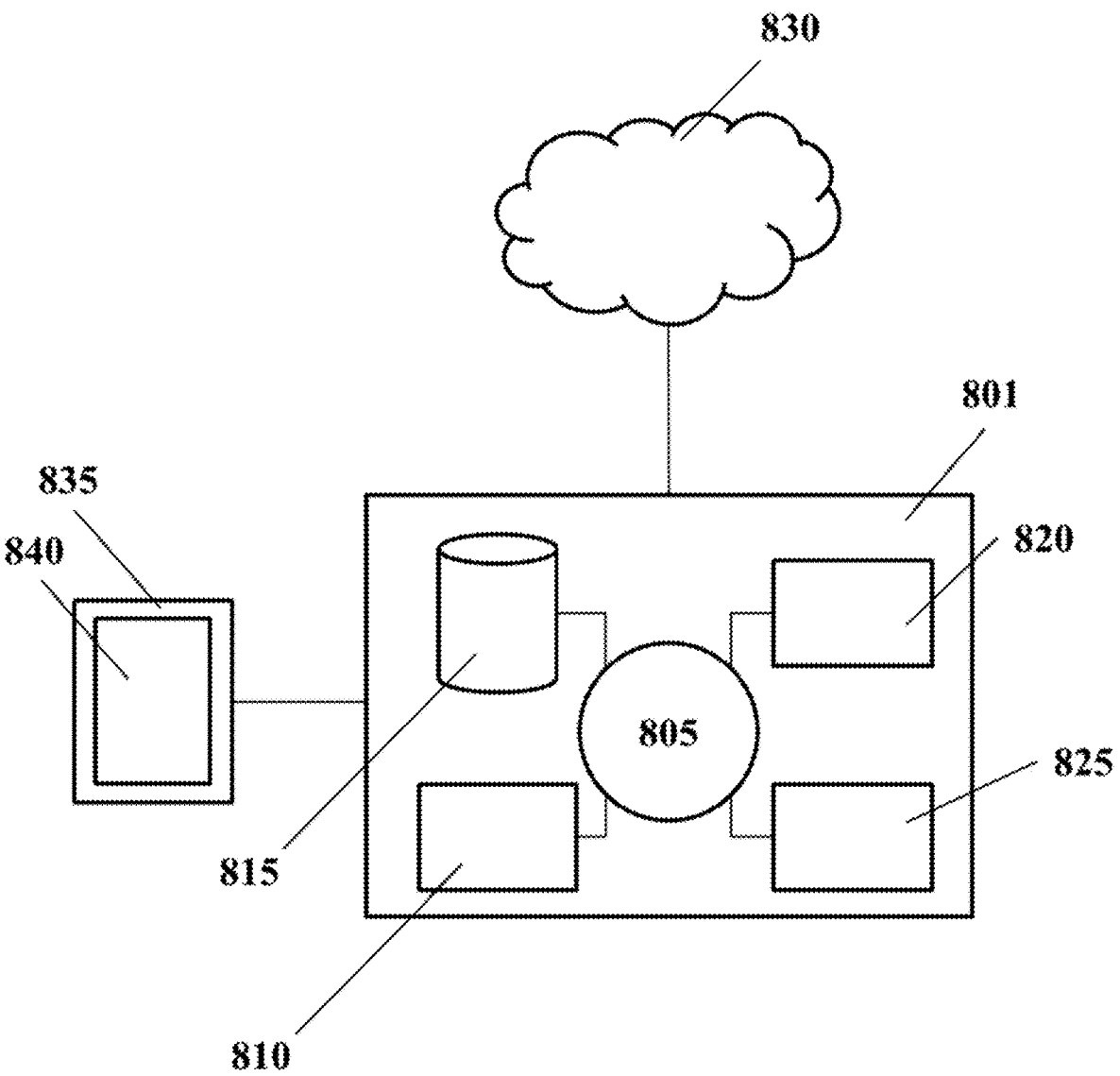
FIG. 8 shows a computer system that is programmed or otherwise configured to perform one or more functions or operations of the present disclosure, such as for example controlling a surgical operation on a subject.

The present disclosure provides computer systems that are programmed to implement methods of the disclosure. FIG. 8 shows a computer system 801 that is programmed or otherwise configured to perform one or more functions or operations of the present disclosure, such as for example controlling a surgical operation on a subject. The computer system 801 can regulate various aspects of methods and systems of the present disclosure, such as, for example, controlling a surgical operation on a subject. The computer system 801 can be an electronic device of a user or a computer system that is remotely located with respect to the electronic device. The electronic device can be a mobile electronic device.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet.

The network 830 in some cases is a telecommunication and/or data network. The network 830 can include one or more computer servers, which can enable distributed computing, such as cloud computing. For example, one or more computer servers may enable cloud computing over the network 830 ("the cloud") to perform various aspects of analysis, calculation, and generation of the present disclosure, such as, for example, administering psychotherapy to the subject. Such cloud computing may be provided by cloud computing platforms such as, for example, Amazon Web Services (AWS), Microsoft Azure, Google Cloud Platform, and IBM cloud. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC). The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., a mobile device of the user). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods provided herein can be implemented by way of machine (e.g., computer processor) executable code stored on an electronic storage location of the computer system 801, such as, for example, on the memory 810 or electronic storage unit 815. The machine-executable or machine-readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.]

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer-readable media may be involved in carrying one or more sequences of one or more instructions to a processor for execution.

The computer system 801 can include or be in communication with an electronic display 835 that comprises a user interface (UI) 840 for providing, for example, an audiovisual representation of a surgical operation. Examples of user interfaces include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, control a surgical operation on a subject.

Force Estimation

Figure 9:
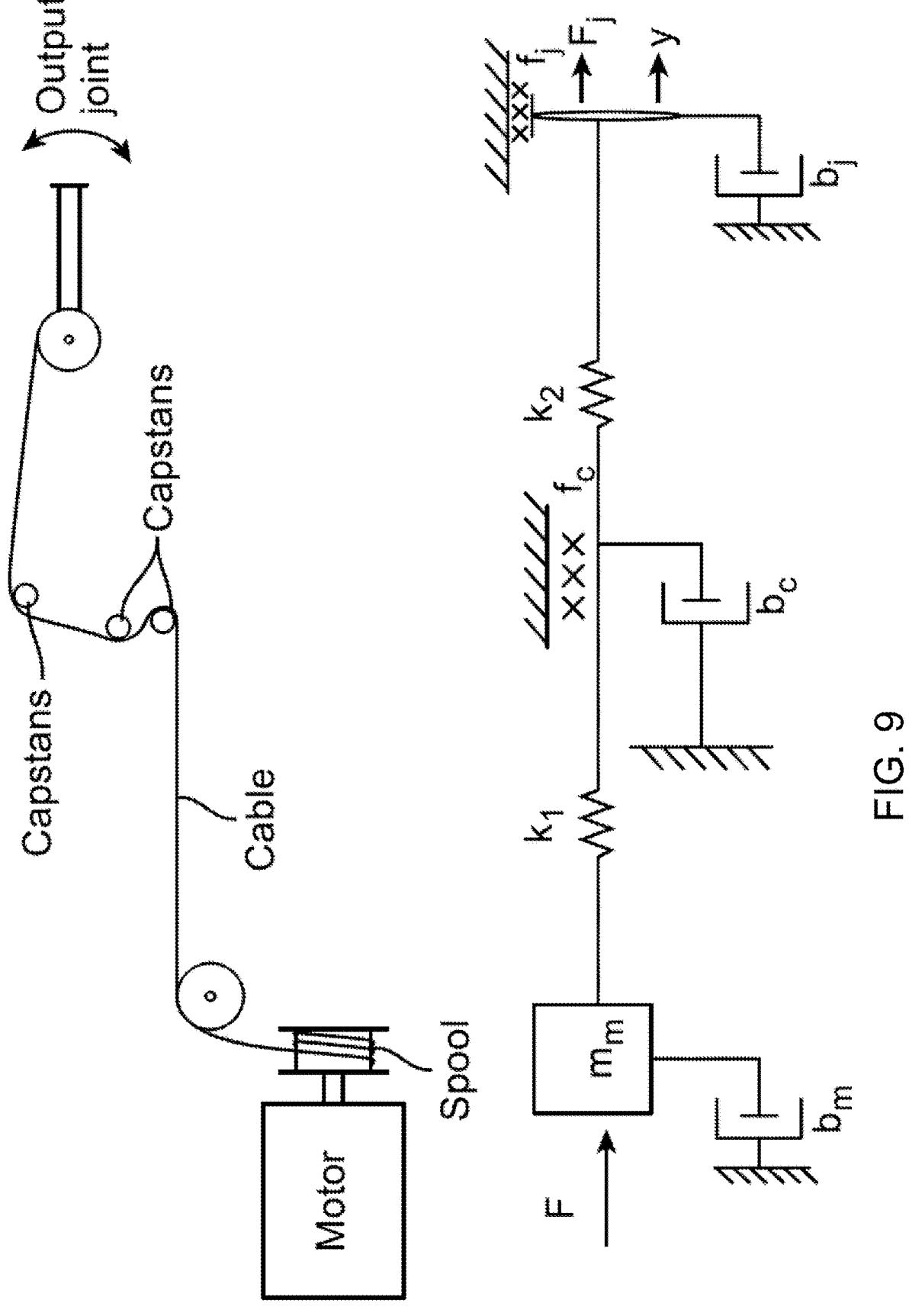
FIG. 9 shows an example of a lumped-parameter model that represents the motor-cable transmission of a cable-driven surgical robotic system.

In some embodiments, estimating an output force applied at an end effector may comprise measuring the force applied at the motor and performing a dynamical simulation that takes into account inefficiencies and other dynamics along the cable path. For example, as shown in FIG. 9, the motor-cable transmission of the cable-driven surgical robotic system (top) is represented as a lumped-parameter model (bottom), where all elements are represented by linear elements.

In some cases, the output force applied at the output joint (e.g., end effector) ($F_j$) may not be directly measurable, but can be estimated using the lumped-parameter model to predict this force based on inputs such as the measured electromagnetic force applied by the motor (F) and any other known states of the system. For example, there may be several elements that affect the relationship between motor force and output joint force. First, this motor force may interact with the motor dynamics, which may include the motor rotor inertia ($m_m$) and motor damping ($b_m$). Second, additional frictional and/or damping losses can occur anywhere along the cable in any number of places, but may be represented in FIG. 9 as a single lumped damping ($b_c$) and friction ($f_c$) to represent the friction and damping at the capstans in the middle of the cable. In some embodiments, the cable may be modeled as an arbitrarily large number of sections in series to further approximate the potentially continuous system. In this example, the cable sections have stiffnesses $k_1$ and $k_2$. Third, the joint itself may have its own additional friction and damping, represented by $f_j$ and $b_j$ respectively.

Determining an estimate of the forces along the cable, and therefore at the joint, may comprise determining or estimating kinematic parameters of the cable (e.g., velocity, acceleration, etc.). For example, kinematic parameters may be determined by sensor measurements, when feasible or practical, such as at the joint and the motor, to obtain the states needed to compute forces. However, it may not be practical to build in sensors at certain locations, such as along the cable length. Therefore, the dynamical simulation may implicitly estimate the values of certain kinematic parameters (e.g., frictional and damping losses along the cable) as part of its primary goal of estimating output force at the output joint.

In some embodiments, extensive system identification tests may be performed to determine or estimate appropriate values for system parameters (e.g., $b_m$, $f_c$, $k_1$, etc). In these tests, observed or known external forces and/or position profiles may be applied at the motor, at known positions along the cable, and/or at the output joint. Forces may be measured as a function of the kinematics to determine the values of these system parameters.

Once the model parameters have been identified, a dynamical simulation may be performed during use of the cable-driven surgical robotic system. The dynamical simulation may process as input data a set of all observed or known values of the system, such as motor positions, motor forces, output joint positions (y), and other measured kinematics and dynamics of the system. The model can then determine an estimated output force $F_j$.

Once the joint forces $F_j$ or the equivalent Torques $T_j$ are determined or estimated, these can be used to determine or estimate the end effector forces and moments $T_j=(JT)*f$, where f denotes the vector of forces and moments at the end effector, and $T_j$ denotes the vector of all joint torques as determined above.

This determined or estimated force f can now be used to communicate to the user how much output force was applied by the cable-driven surgical robotic system at the output joint. In some embodiments, such communication (e.g., indicative of the forces and/or moments being applied by or to the end effector) may be provided via an audiovisual representation of feedback to a user of the surgical robotic system. Therefore, methods and systems of the present disclosure may determine and provide an audiovisual representation of an output force that takes into account more robot dynamics than just the quasi-static cable stretch, thereby providing increased accuracy and reliability of user operation of the surgical robotic system.

Figure 10:
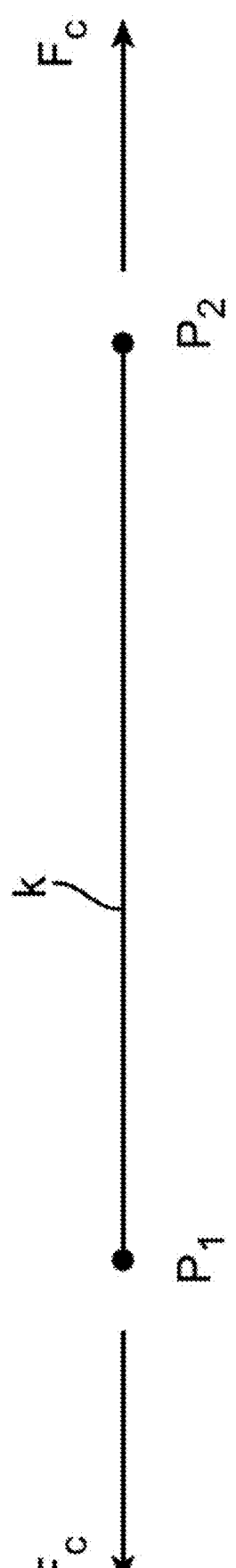
FIG. 10 shows an example of a compliant member with stiffness k, and the absolute positions of each end $P_1$ and $P_2$, with the force acting on the cable, Fc.
Figure 10:
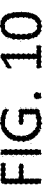

FIG. 10 shows an example of a compliant member with stiffness k, and the absolute positions of each end $P_1$ and $P_2$, with the force acting on the cable, $F_c$. In some embodiments, the external force acting on one or more output joints of a robot can be estimated by utilizing two position sensors and a compliant member of known parameters such as stiffness. This may be based on a principal that if there is a compliant member and the position of both ends of the compliant member are known, then the force being transmitted through that member can be estimated, if basic properties such as the stiffness of the material are known. This can be represented by the formula $F=k(P_2-P_1)$, where F is the external force acting on the member, k is the stiffness of the member, $P_1$ is the absolute position of the first end of the member, and $P_2$ is the absolute position of the second end of the member. In some embodiments, the member can be a semi-rigid member in which both compression and tension forces can be applied. In other embodiments, the member comprises a cable or wire in which only tension can be applied. In still other embodiments the member can only exert compression forces (loose media or a brittle material or concrete).

In a cable-driven surgical robotic system, this formula can be used to estimate the output force that each motor is applying to each cable. Then, using the mechanics of the specific output joint, the output force that the system is applying externally with that output joint can be determined or estimated. In the same way (e.g., based on Newton's third law), it can be used to estimate the force that an external entity applies on that same output joint (e.g., a reaction force applied by a body part, such as a tissue, of a subject on the output joint).

This method may be used in systems using any number of cables on an output joint, in which the kinematics and/or mechanics of the system are solvable, as long as the position of each joint is individually measured and the stiffness of each cable is known. Therefore, methods and system of the present disclosure may be applied in cases where a joint is driven by one member or cable, two members or cables, three members or cables, etc. It also can be utilized where 3 cables are used to drive 2 joints, 4 cables are used to drive 3 joints, 5 cables are used to drive 4 joints, etc.

The position of each end of the compliant member can be measured using a variety of methods, such as various sensor measurements, e.g., potentiometers, optical encoders, interferometry, ultrasound, light detection and ranging (Lidar) sensors, accelerometers, inertial measurement unit (IMU) sensors, magnetometers, image sensors, optical sensors, etc.

Figure 11:
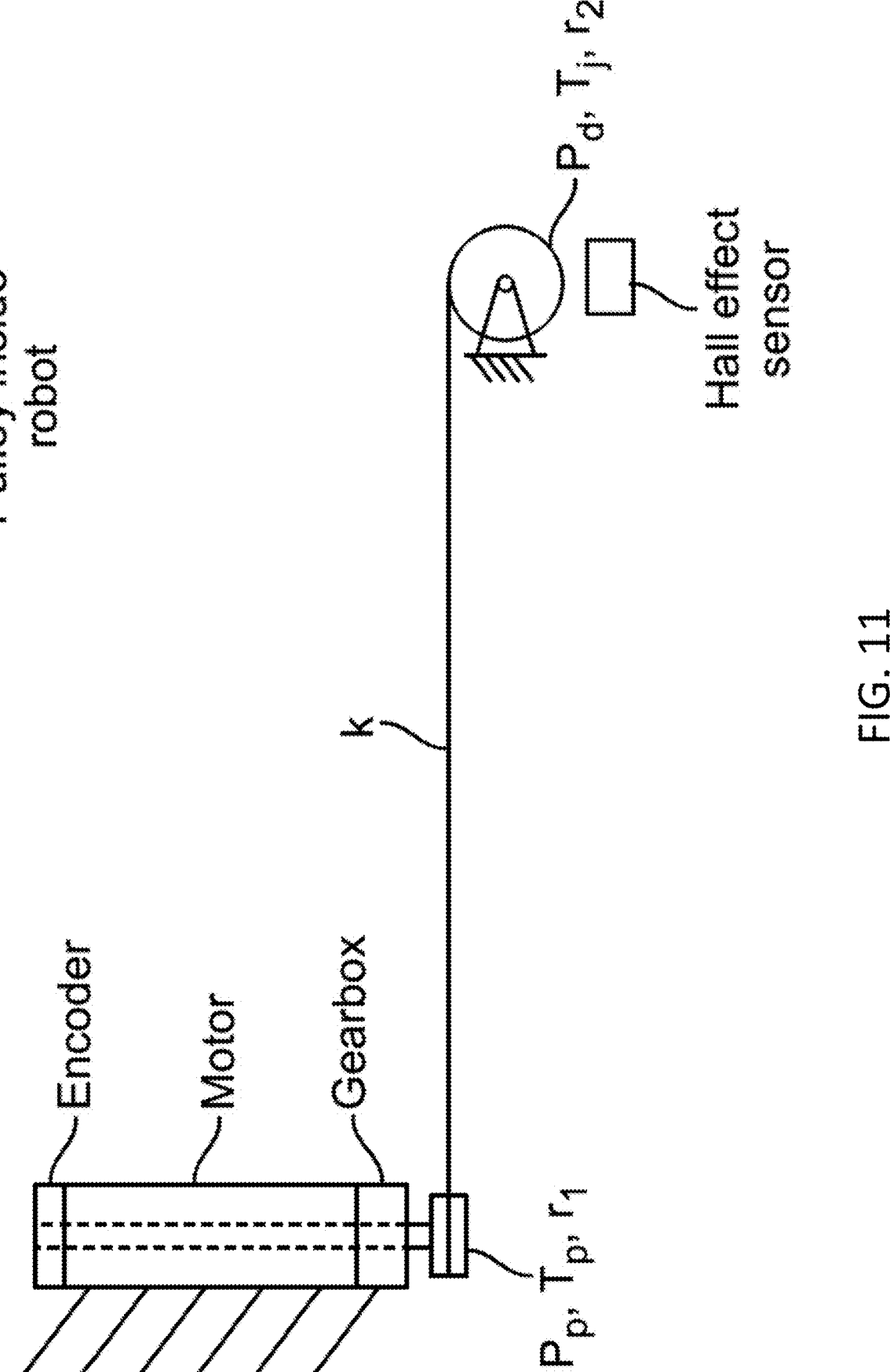
FIG. 11 shows an example representation of a cable-driven robotic system.

FIG. 11 shows an example representation of a cable-driven robotic system. In some embodiments, an encoder is positioned on the shaft of a motor that is connected to a gearbox that is connected to a pulley that is connected to the compliant cable. The position of the cable can be measured and tracked by using the optical encoder by utilizing the following general formula. $P_p=P_c*R*r_1$, where $P_p$ is the position of the proximal end of the cable, $P_c$ is the angular position of the motor shaft (in radians or Rad) as measured by the encoder, R is the gear ratio of the gearbox, $r_1$ is the radius of the cable pulley. This estimate may be more accurate when there is minimal backlash or compliance in the gearbox. In other embodiments, an encoder can be attached directly to the cable pulley and the position of the end of cable can be estimated using the following general formula, $P_p=P_c*r_1$.

In some embodiments, the position of the other end (distal end) of the cable can be measured with a Hall-effect sensor array embedded into the drive pulley of the robot joint inside the patient. This can be calculated using the following formula, $P_d=P_h*r_2$, where $P_d$ is the position of the distal end of the cable, $P_h$ is the position of the joint measured by the Hall-effect sensor array (in radians or Rad) and $r_2$ is the radius of the drive pulley of the joint.

The external force being applied to the cable can then be calculated as $F_c=k(P_d-P_p)$, where $F_c$ is the external force applied to the cable, k is the stiffness of the cable, $P_p$ is the proximal position of the cable, and $P_d$ is the distal position of the cable.

The stiffness of the cable or member is a function of the material stiffness (Young's modulus), cross-sectional area and the length of the cable or member.

In some embodiments, $P_d$ and $P_p$ may be zeroed (calibrated and/or normalized) relative to some start state, such that $P_d$ and $P_p$ are measured relative to that starting zero position. It may be important to ensure that there are no external forces upon startup during this process.

Figure 12:
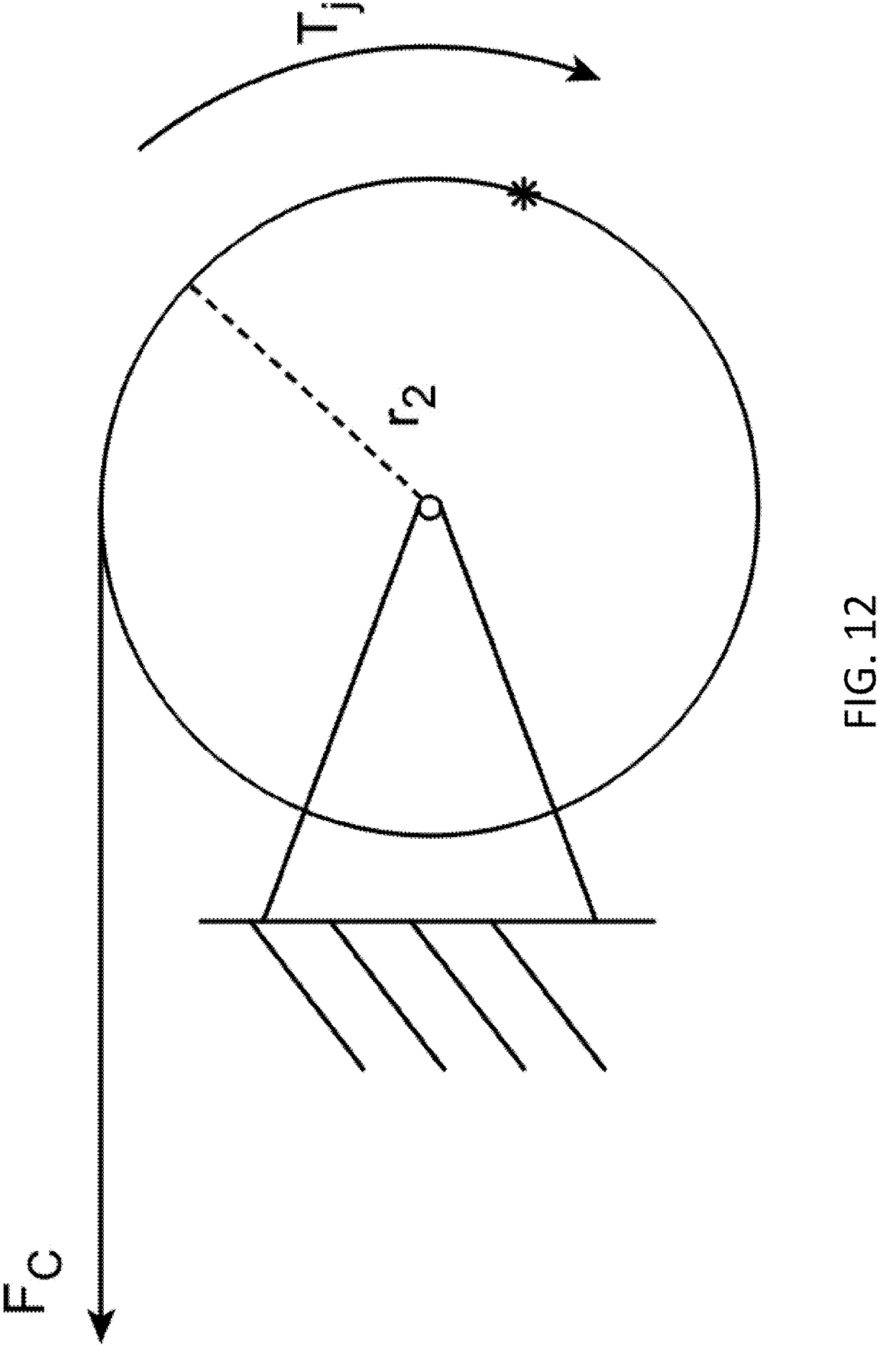
FIG. 12 shows an example of a free body diagram of a joint drive pulley controlled by one cable with external torque $T_j$ applied to the joint.

FIG. 12 shows an example of a free body diagram of a joint drive pulley controlled by one cable with external torque $T_j$ applied to the joint. In some embodiments, where there is one cable controlling one joint, the torque acting on the joint can be calculated from the force acting on the cable with the following formula, $Tj=Fc*r_2$, where Tj is the torque acting on the joint.

Figure 13:
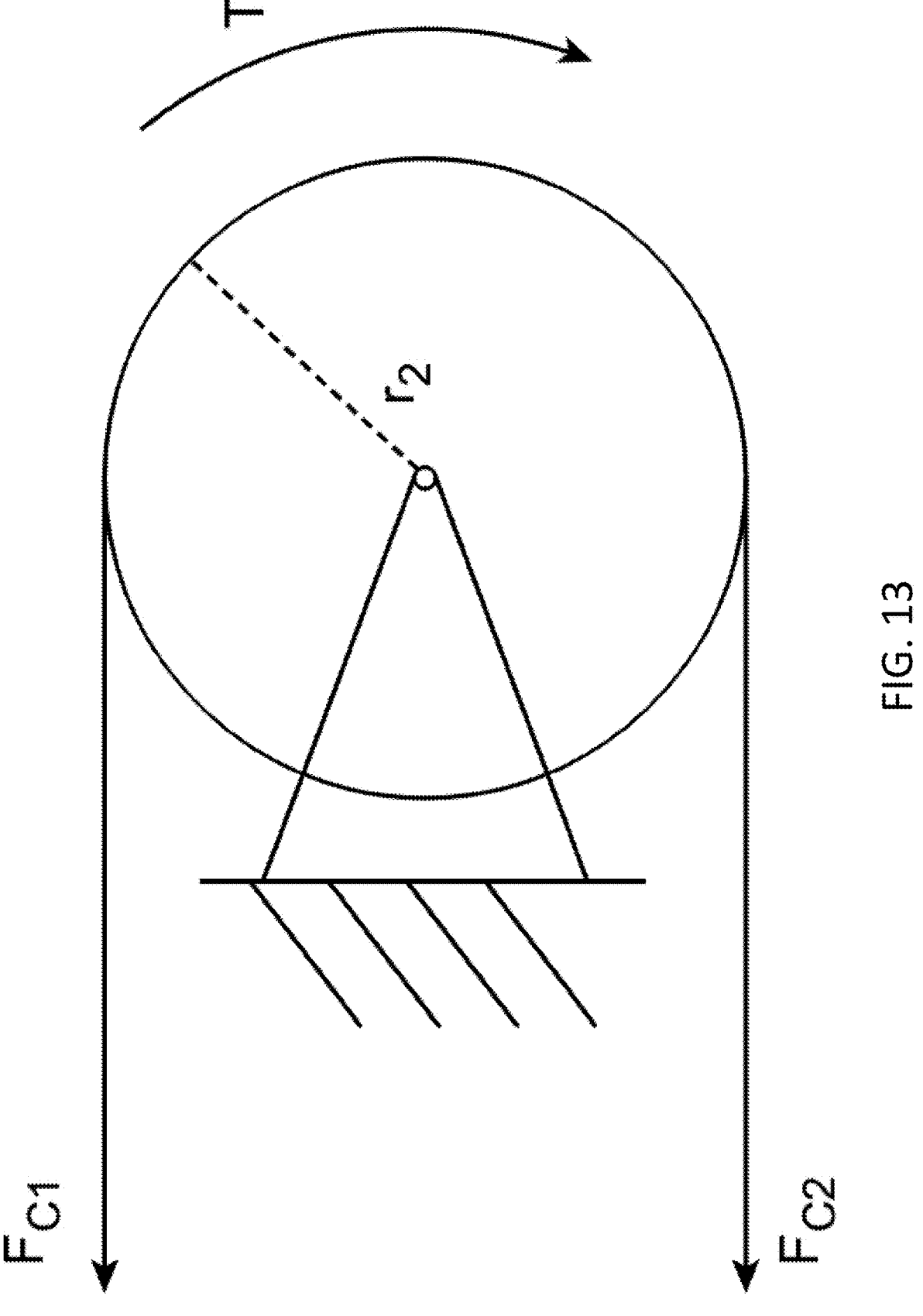
FIG. 13 shows an example of a free body diagram of a joint drive pulley controlled by two cables with external torque $T_j$ applied to the joint.

FIG. 13 shows an example of a free body diagram of a joint drive pulley controlled by two cables with external torque $T_j$ applied to the joint. In some embodiments, there are two cables controlling one joint. In this embodiment the external forces acting on each cable can be measured via the methods described above, $F_{c1}=k_1(P_{d1}-P_{p1})$ and $F_{c2}=k_2(P_{d2}-P_{p2})$, where $F_{c1}$ is the external force acting on cable 1, $k_1$ is the stiffness of cable 1, $P_{d1}$ is the position of the distal end of cable 1, $P_{p1}$ is the position of the proximal end of cable 1, $F_{c2}$ is the external force acting on cable 2, $k_2$ is the stiffness of cable 2, $P_{d2}$ is the position of the distal end of cable 2, $P_{p2}$ is the position of the proximal end of cable 2. The total force acting on that one joint can then further be calculated using the following formula: $F_t=F_{c2}-F_{c1}$, where $F_t$ is the total force acting on the joint. The torque acting on the joint can be calculated utilizing the same formula as above.

Using this method, the torque acting on each joint of a surgical robot can be estimated. Combining this state knowledge with the kinematic state of the robot the external forces acting on any part of the robot can be estimated including the magnitude and the direction of the force. It is important to note that this may generally work to estimate the total of external forces being applied and may break down when multiple external forces are acting on the arm at different locations on the arm.

This can be used to wrap a control loop around the force being applied on a cable, limit the force that the robot can externally apply on tissue for safety reasons or even enable us to change our controls schema such that we can enable different force modes. It also may be able to provide an input to a haptic device to provide force feedback to the user so that the user can better understand how much force they are applying to what is being worked on.

Figure 14:
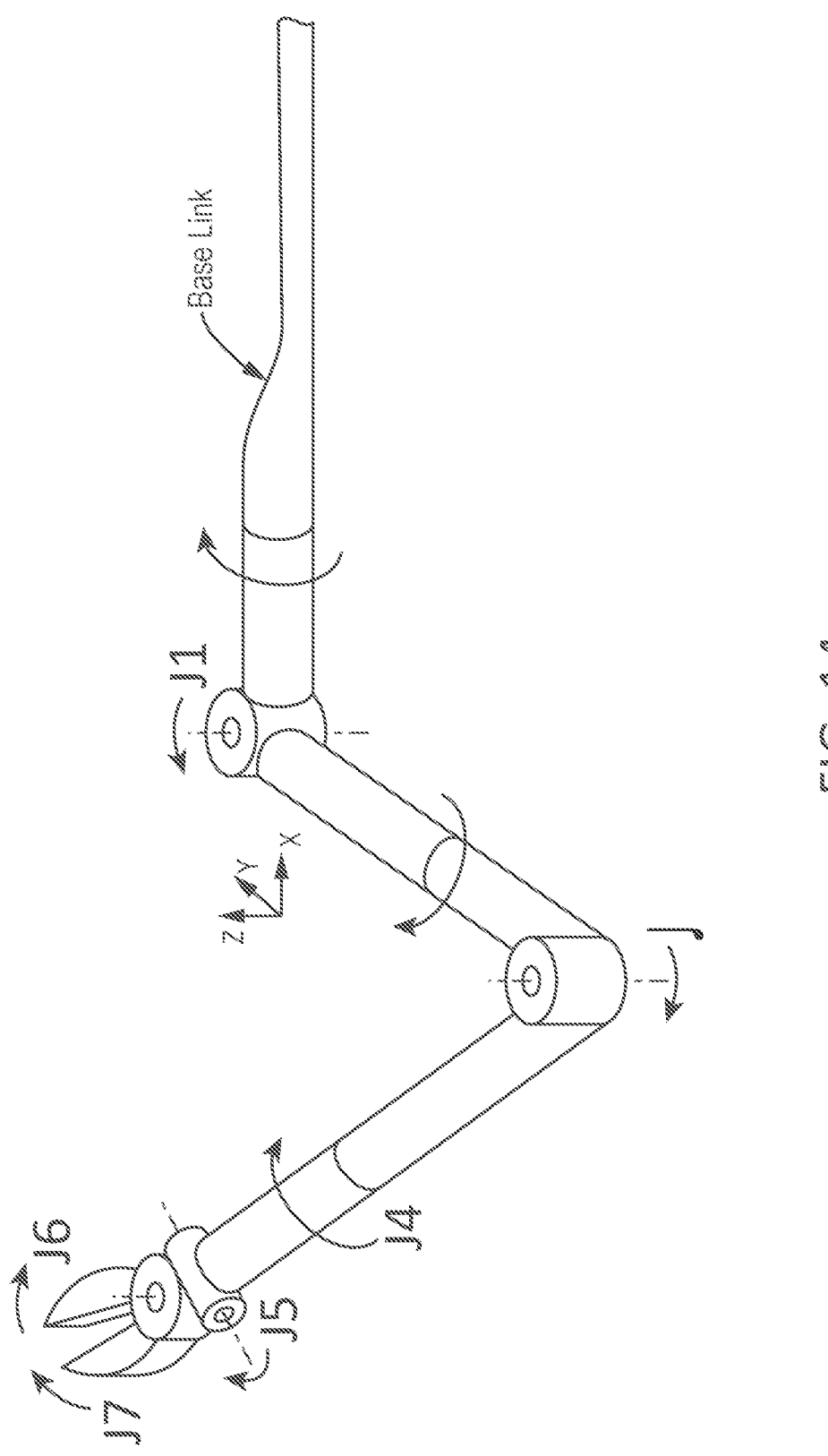
FIG. 14 shows an example of a robotic arm with a base link and seven joints that provide movement in multiple degrees of freedom.

FIG. 14 shows an example of a robotic arm with a base link and seven joints that provide movement in multiple degrees of freedom. Since the weight of the drive cables may be negligible, and the cables may be operated with pretension that brings the cables in the linear range, the cables can be considered nearly lossless transmission elements with a constant (e.g., static) stiffness during the robot operation. The force applied at the joint, $F_j$, can be determined using the expression: $F_j=F-f_c-f_j$.

Further, the inverse dynamics of the robotics arm may be modeled using the expression: $T=M(q) \, q_{dot\text{-}dot}+C(q) \, q_{dot}+G(q)+J^T F_{tip}$. Here, as shown in FIG. 14, $F_{tip}$ denotes the force applied by the robot at the tip (e.g., end effector); and q, $q_{dot}$, and $q_{dot\text{-}dot}$ denote vectors containing joint angles, velocities, and accelerations, respectively. Under quasi-static conditions of low speeds and accelerations, the joint torques T map to the $F_{tip}$ as given in the following expression: $T=G(q)+J^T F_{tip}$.

Visual Feedback

Haptic feedback may be used in surgical robotics systems to provide a user (e.g., surgeon) of the surgical robotic system with a physical sensation in order to convey certain useful or critical information to the driving of the robotic system. For example, haptic feedback may be used to help the user understand how much force they are imparting on the environment with the robotic system and where. As another example, haptic feedback may be used to help the user understand how much force the environment is imparting on the robotic system and where. As another example, haptic feedback may be used to indicate proximity to or contact with objects in the environment and where. As another example, haptic feedback may be used to communicate a physical limitation of the system or of an environmental boundary or even be used to provide guidelines to the user.

In some surgical robotic systems, there exists input devices with mechanical linkages and actuators that may be controlled and coordinated to provide direct haptic feedback. However, these input devices may face challenges owing to their high complexity and resulting high cost. Thus, many surgical robotics systems opt to use other simpler input devices; therefore, due to the architecture of those input devices, such surgical robotics systems may be incapable of directly or physically providing that haptic feedback. An example of this is demonstrated in systems that use a free floating game controller styled hand controller. Such systems may be limited to simple vibratory haptic feedback, which may be insufficiently detailed to communicate both the magnitude and direction of many desired types of haptic feedback. Recognizing the need for improved audiovisual feedback, systems and methods of the present disclosure provide visual (e.g., direction and magnitude) feedback to the user without the need for direct haptic feedback. In some embodiments, such visual feedback may be presented to the user in conjunction with haptic feedback.

In some embodiments, systems and methods of the present disclosure comprise a visualization system configured to present to the user, live imagery of the worksite. The system may take in the live imagery from the visualization source and pass the data through a processor that is capable of overlaying additional data or virtual objects on top of the live imagery. After the imagery is processed and any desired overlays have been added, the imagery may be presented to the user in the desired format. In some embodiments, the imagery is presented to the user via a 2-D display. In some embodiments, the imagery is presented to the user via a 3-D display. In some embodiment, the imagery is presented to the user via a 3-D head-mounted display. In some embodiments, the imagery is presented to the user via a peer-in stereoscopic display.

In some embodiments, a processor of the surgical robotics system further receives and processes data from other sources to determine the scale, location, orientation, or other attributes of the virtual objects to be overlaid onto the live imagery.

In some embodiments, the processor is provided with the magnitude and direction of the force that the robotic system is applying to the environment as well as the position state of the entire robot. In some embodiments, the processor scales the length of a virtual arrow based at least in part on the magnitude of the force being applied and maps the orientation of the arrow to the direction that the force is being applied. In some embodiments, the process utilizes the position state of the robotic system to map the position of virtual arrow to the tip of the robotic end-effector. The result is that the user sees a virtual arrow that is stuck or coupled to their end-effector, having a size and direction which indicates to the user how much force they are applying and in what direction.

In some embodiments, the position of the end-effectors is calculated utilizing computer vision techniques. In some embodiments, there is a minimum threshold for magnitude of force below which the arrow does not appear for the user. In some embodiments, the opacity of the virtual arrow is also scaled with the magnitude of the force. In some embodiments, the arrow is virtually attached to different elements of the robotic system within the field of view of the imagery. In some embodiments, the virtual arrow is shown in some fixed location on the imagery. In some embodiments, the virtual overlay takes the form of any other geometrical form that may be readily used to communicate both magnitude and direction. In some embodiments, the virtual arrow is utilized to communicate direction but the magnitude is communicated via another geometric entity such as a bar, the size of which is scaled with the magnitude. In some embodiments, the virtual arrow is utilized to communicate direction, but the magnitude is communicated via a transparent colored overlay coming from outside of the imagery, the opacity of which is scaled with the magnitude of the force applied. In some embodiments, the virtual arrow is utilized to communicate direction, but the magnitude is communicated via an overlaid number or text adjacent to the arrow. In some embodiments, the geometry of the virtual object may change based at least in part on the magnitude or direction of the input.

In some embodiments, the processor receives and processes data from a proximity sensor or contact sensor embedded in a robotic arm, and scales the magnitude of the virtual arrow based at least in part on proximity and the direction of the arrow to indicate the direction of the proximity. In some embodiments, the color of the arrow may be changed to indicate contact. In some embodiments, the virtual object may be changed to a different object to indicate contact.

In some embodiments, the processor receives and processes data defining a particular target position or orientation of the end-effector, scales the magnitude of the virtual arrow based at least in part on the distance from that desired target, and sets the orientation of the virtual arrow based at least in part on the direction that the user has to translate the end-effector to reach the desired target.

In some embodiments, where there is also a desired orientation of the end-effector, additional overlays such as curved virtual arrow may be utilized to indicate to the user which direction they may rotate the end-effector in order to achieve the desired end-effector orientation. This sort of guided movement may be useful for engagement with the robotic system or for AI-guided or AI-assisted surgery.

In some embodiments, the processor receives and processes data from a virtual boundary and scales the magnitude of the virtual arrow based at least in part on proximity to that boundary and controls the orientation of the arrow based at least in part on the vector that represents the minimum normal distance to that boundary. In some embodiments, that boundary may be created by the user ahead of time in order to protect certain biological features. In some, that boundary may be automatically created by the system (e.g., utilizing computer vision techniques) to outline anatomical features. In some embodiments, the computer vision-created anatomical boundary may be analyzed by a trained machine learning algorithm to identify critical anatomy, and the boundary may be augmented to provide further protection for those elements.

Figure 15:
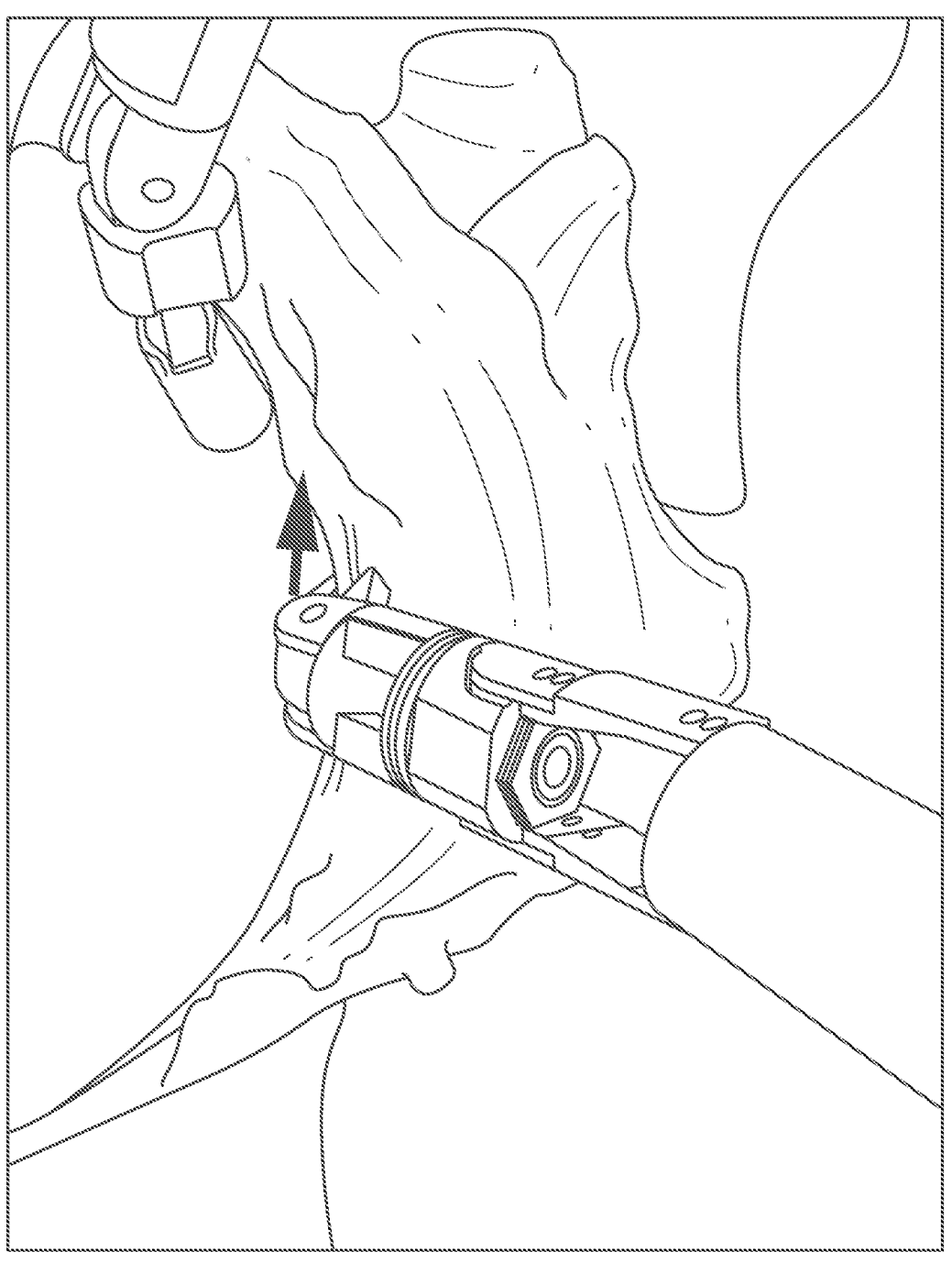
FIG. 15 shows an example of a surgical robotic system that provides visual feedback during a surgical operation within an internal cavity of a subject.

FIG. 15 shows an example of a surgical robotic system that provides audiovisual feedback during a surgical operation within an internal cavity of a subject.

Methods and systems of the present disclosure may perform error tracking of the cable-driven surgical robotic system. For example, a variable indicative of robot tracking error can be determined (e.g., continuously, in real time, or in near real time). The tracking error can be expressed as the difference (e.g., delta) in position and/or orientation between where the controllers actually are (e.g., "matching human") and the position and/or orientation where the sensor measurements are indicating the robot is (e.g., the "sensed" position and/or orientation based on sensor measurements such as Hall-effect sensors and rail encoders). As a note, the "sensed" position and/or orientation may contain errors or impreciseness relative to the true position and/or orientation of the robot, arising from factors such as bending and vibration in the support arms, error in the sensor measurements, etc. Tracking error intensity values may be determined, estimated, and/or tracked for position and/or orientation, and a threshold may be applied to determine when to display such errors to a user (e.g., on a display for a surgeon to view). For example, error or alarm events may be triggered when a tracking error meets or exceeds a pre-determined threshold.

Positional tracking error may be caused by various factors. For example, a surgeon may move faster than the surgical robot can move, which can cause overshoot. In another example, the surgeon may press or drive a surgical arm into an object, such as a tissue of the subject or other parts of the robot (e.g., camera, support arms, etc.), which can injure the subject but can also cause the integrator to wind up causing large unintended motions. As another example, the surgeon can pull on an object (e.g., a suture), in which the amount of force applied is proportional to the tracking error, which causes potentially large unintended motions upon releasing the pull on the object (e.g., the gripper is opened or the suture breaks).

Orientation tracking error may be caused by various factors. For example, the surgeon may have grasped an object (e.g., a tissue or a suture in a tissue) and is attempting to rotate the grasper but it does not produce the intended movement or rotation, which can cause potentially large unintended motions (e.g., if the suture suddenly slips free of the tissue). As another example, the surgeon may be attempting to rotate a grasper while an object is obstructing or blocking movement or rotation of the grasper's arm.

In some embodiments, the display provides an audiovisual representation of a virtual controller model (e.g., a Polhemus shaped 6 degrees-of-freedom indicator, which may be located at the bottom of the screen on the left and/or right) which corresponds to the arm(s) generating the error. Positional error may be visually indicated by a second controller model drawn with respect to the reference controller model, with a dashed line drawn between the two controller models. Orientation error may be visually indicated by arrows surrounding the reference controller model.

The robot tracking error display may show a reference controller having a first color (e.g., green) that is the same shape as the actual controller that the surgeon is holding. A second controller having a second color (e.g., white) may be shown at an offset, which is visually indicative of the direction and/or magnitude of the positional error. In some embodiments, rotational error is visually indicated by curved arrows which appear around the second controller.

Figure 16A:
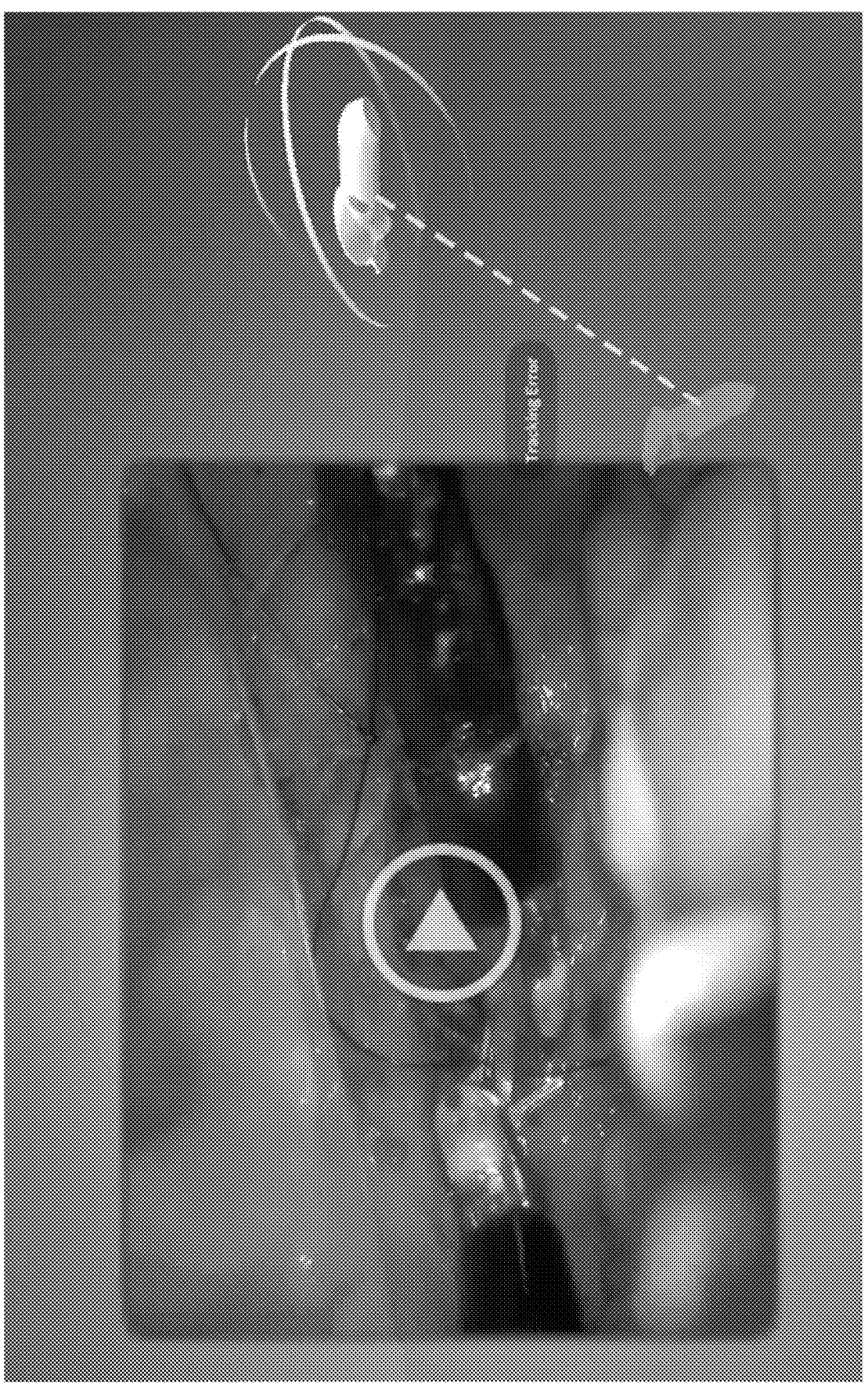
Figure 16B:
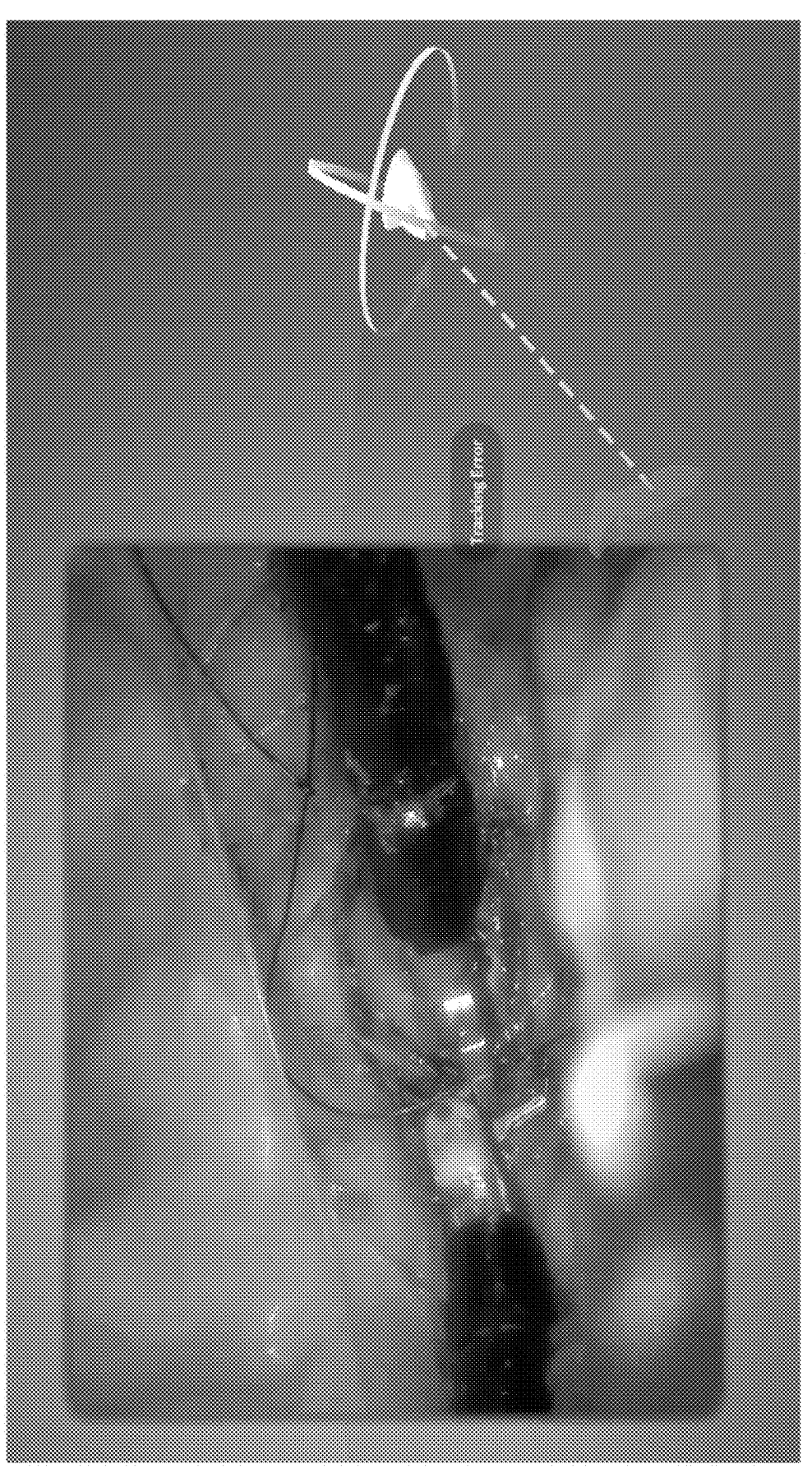
Figure 16C:
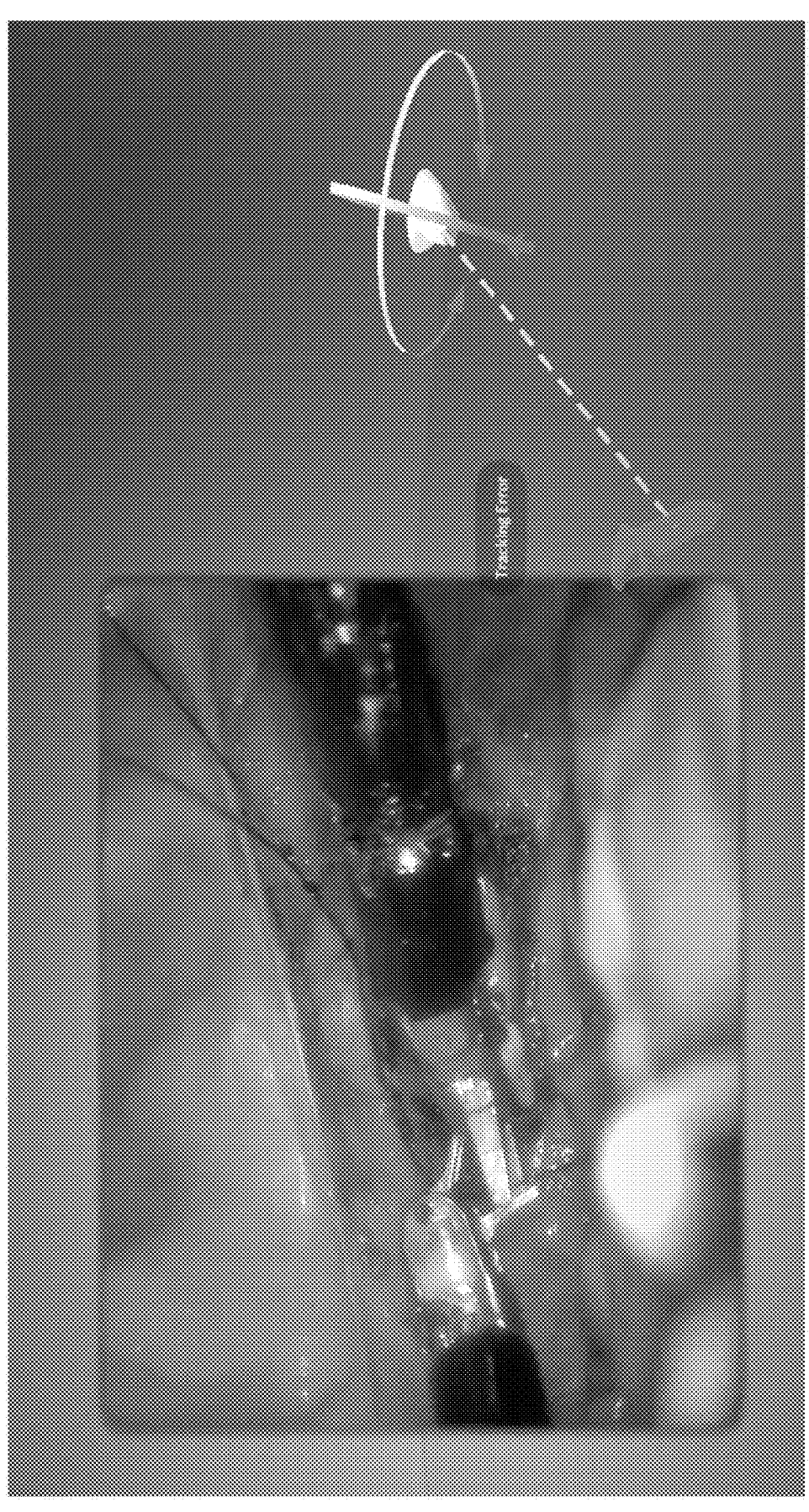
Figure 16D:

FIGS. 16A-16D show examples of an audiovisual representation of a robot error tracking approach which is performed during a surgical operation within an internal cavity of a cadaver. As shown in FIGS. 16A-16C, positional tracking error is visually indicated by a second controller model (shown on the right side) drawn with respect to the reference controller model (shown in the middle of the screen), with a dashed line drawn between the two controller models, while orientation error is visually indicated by arrows surrounding the reference controller model. As shown in FIG. 16D, error tracking in a cadaver is shown with the reference controllers locked to the bottom of the screen.

In some embodiments, audiovisual feedback may be used in combination with other forms of feedback. For example, audiovisual feedback may comprise a combination of visual feedback (e.g., displayed on a screen) and auditory feedback (e.g., beeps, buzzes, alarm sounds, etc.). As another example, audiovisual feedback may be combined with haptic feedback (e.g., direct force, vibratory force, skin stretch, etc.). As another example, audiovisual feedback may be used to enhance other forms of feedback, such as to provide additional context and/or higher resolution feedback. As another example, audiovisual feedback may be used to reinforce other forms of feedback, such as to highlight or redirect attention of a user to the other forms of feedback, or to provide a backup or redundancy to the other forms of feedback.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for determining an output force applied by an output joint of a cable-driven surgical robot, comprising:
    applying, using a motor of the cable-driven surgical robot, a motor force to a cable communicatively connected to the output joint of the cable-driven surgical robot;
    identifying a set of kinematic parameters of a lumped-parameter model, in response to the motor force, wherein the lumped-parameter model is indicative of an interactive structural configuration of the cable-driven surgical robot, wherein the set of parameters comprises at least one joint parameter, at least one cable parameter, and at least one motor parameter, wherein the identifying comprises (i) measuring parameters using at least one sensor or (ii) estimating parameters via dynamical simulation; and
    determining an output force applied by the output joint, wherein the determining comprises performing a dynamical simulation during use of the cable-driven surgical robot using the set of kinematic parameters.

2. The method of claim 1, further comprising computer processing the motor force and the output force.

3. The method of claim 2, wherein the computer processing comprises comparing the motor force and the output force.

4. The method of claim 2, wherein the computer processing comprises determining a difference between the motor force and the output force.

5. The method of claim 2, further comprising adjusting the motor force applied to the cable based at least in part on the computer processed motor force, output force, or both.

6. The method of claim 5, wherein the adjusting is performed in real time or in substantially real time.

7. The method of claim 1, wherein the set of kinematic parameters comprises at least one static parameter and one dynamic parameter.

8. The method of claim 7, wherein the at least one static parameter comprises position, orientation, length, width, height, diameter, or stiffness.

9. The method of claim 8, wherein the at least one static parameter comprises at least one of: a static parameter of the motor, a static parameter of the cable, and a static parameter of the output joint.

10. The method of claim 7, wherein the at least one dynamic parameter comprises damping, fraction friction, velocity, acceleration, or inertia.

11. The method of claim 10, wherein the at least one dynamic parameter comprises at least one of: a dynamic parameter of the motor, a dynamic parameter of the cable, and a dynamic parameter of the output joint.

12. The method of claim 1, further comprising applying the output force to a body part of a subject using the output joint.

13. The method of claim 12, further comprising determining a reaction force exerted by the body part of the subject on the output joint.

14. The method of claim 13, further comprising adjusting the motor force applied to the end effector based at least in part on the determined reaction force.

15. The method of claim 1, wherein the at least one sensor comprises one or more of a camera, a position sensor, an accelerometer, a magnetic sensor, light sensor, or combinations thereof.

16. The method of claim 1, further comprising generating an audiovisual representation of the output force, wherein the audiovisual representation comprises a virtual object comprising at least one discrete or continuous variable that is dynamically changing based at least in part on the determined output force.

17. The method of claim 16, further comprising displaying the virtual object on a screen or display.

18. The method of claim 17, further comprising generating and displaying an overlay of the virtual object onto an image captured by at least one camera.

19. The method of claim 1, wherein the cable-driven surgical robot is partially or wholly inside of a cavity of a body of a subject.

20. The method of claim 1, wherein the cable-driven surgical robot is wholly inside of a cavity of a body of a subject.

21. A computer-implemented system for determining an output force applied by an output joint, comprising:
    a cable-driven surgical robot comprising a motor, the output joint, and a cable communicatively connected to the output joint; and
    one or more computer processors operatively coupled to the cable-driven surgical robot, wherein the one or more computer processors are individually or collectively programmed to:
    apply, using the motor, a motor force to the cable;
    identify a set of kinematic parameters of a lumped-parameter model, in response to the motor force, wherein the lumped-parameter model is indicative of an interactive structural configuration of the cable-driven surgical robot, wherein the set of parameters comprises at least one joint parameter, at least one cable parameter, and at least one motor parameter, wherein the identifying comprises (i) measuring parameters using at least one sensor or (ii) estimating parameters via dynamical simulation; and determine an output force applied by the output joint, wherein the determining comprises performing a dynamical simulation during use of the cable-driven surgical robot using the set of kinematic parameters.

\* \* \* \* \*